US008478605B2

(12) United States Patent
Miller et al.

(10) Patent No.: US 8,478,605 B2
(45) Date of Patent: Jul. 2, 2013

(54) APPROPRIATENESS OF A MEDICATION THERAPY REGIMEN

(75) Inventors: Scott A. Miller, Palatine, IL (US); Carl Bertram, Downers Grove, IL (US)

(73) Assignee: Walgreen Co., Deerfield, IL (US)

( * ) Notice: Subject to any disclaimer, the term of this patent is extended or adjusted under 35 U.S.C. 154(b) by 1035 days.

(21) Appl. No.: 11/458,075

(22) Filed: Jul. 17, 2006

(65) Prior Publication Data

US 2008/0097784 A1      Apr. 24, 2008

(51) Int. Cl.
*G06Q 50/00* (2012.01)
(52) U.S. Cl.
USPC .................................... 705/2; 705/3
(58) Field of Classification Search
USPC ........................................... 705/2, 3
See application file for complete search history.

(56) References Cited

U.S. PATENT DOCUMENTS

| | | | |
|---|---|---|---|
| 4,766,542 A | 8/1988 | Pilarczyk ..................... 364/413 |
| 5,016,172 A | 5/1991 | Dessertine ............... 364/413.02 |
| 5,612,869 A | 3/1997 | Letzt et al. ..................... 395/203 |
| 5,666,492 A | 9/1997 | Rhodes et al. ..................... 705/3 |
| 5,737,539 A | 4/1998 | Edelson et al. |
| 5,758,095 A | 5/1998 | Albaum et al. |
| 5,845,255 A | 12/1998 | Mayaud |
| 5,860,917 A | 1/1999 | Comanor et al. |
| 5,924,074 A | 7/1999 | Evans |
| 5,976,082 A | 11/1999 | Wong et al. |
| 6,000,828 A | 12/1999 | Leet .............................. 364/401 |
| 6,014,631 A | 1/2000 | Teagarden et al. ................. 705/3 |
| 6,029,138 A | 2/2000 | Khorasani et al. |
| 6,081,786 A | 6/2000 | Barry et al. ....................... 705/3 |
| 6,161,095 A | 12/2000 | Brown |
| 6,219,674 B1 | 4/2001 | Classen |
| 6,240,394 B1 | 5/2001 | Uecker et al. |
| 6,305,377 B1 | 10/2001 | Portwood et al. ............. 128/897 |
| 6,317,719 B1 | 11/2001 | Schrier et al. |
| 6,356,873 B1 | 3/2002 | Teagarden et al. ................ 705/3 |
| 6,397,190 B1 | 5/2002 | Goetz |
| 6,421,650 B1 | 7/2002 | Goetz et al. |
| 6,578,003 B1 | 6/2003 | Camarda et al. |
| 6,584,472 B2 | 6/2003 | Classen |
| 6,587,829 B1 | 7/2003 | Camarda et al. .................. 705/3 |
| 6,612,985 B2 | 9/2003 | Eiffert et al. |
| 6,654,724 B1 | 11/2003 | Rubin et al. ...................... 705/3 |

(Continued)

OTHER PUBLICATIONS

"Discontinuing Antiepleptic Drugs in Patients Who are Seizure Free on Monotherapy", J Neurol Neruosurg Psychiatry 2002; 72:22-25.

(Continued)

*Primary Examiner* — Gerald J. O'Connor
*Assistant Examiner* — Trang Nguyen
(74) *Attorney, Agent, or Firm* — Francis C. Kowalik; Marshall, Gerstein & Borun LLP

(57) ABSTRACT

A method of determining the appropriateness of a medication therapy regimen detects and reduces gaps occurring between established standards of treatment and treatment provided to a person through a medication therapy regimen. Methods of determining the appropriateness of a medication or medication therapy regimen and intervention thereof are provided herein. The methods of determining the appropriateness of a medication and intervention include receiving information on a medication for the person, receiving treatment guidelines for treating a chronic medical condition, determining a level of compliance between the medication and the treatment guidelines, and intervening in a medical treatment of the person if the medication does not comply with the one or more treatment guidelines.

16 Claims, 9 Drawing Sheets

U.S. PATENT DOCUMENTS

| | | | |
|---|---|---|---|
| 6,694,298 B1 | 2/2004 | Teagarden et al. ................ | 705/3 |
| 6,980,958 B1 | 12/2005 | Surwit et al. | |
| 7,574,370 B2 | 8/2009 | Mayaud | |
| 2001/0020240 A1 | 9/2001 | Classen | |
| 2001/0056358 A1 | 12/2001 | Dulong et al. .................... | 705/2 |
| 2002/0002473 A1 | 1/2002 | Schrier et al. ..................... | 705/3 |
| 2002/0010595 A1 | 1/2002 | Kapp | |
| 2002/0042725 A1 | 4/2002 | Mayaud | |
| 2002/0042726 A1* | 4/2002 | Mayaud ............................ | 705/2 |
| 2002/0095314 A1 | 7/2002 | Bodsworth et al. | |
| 2002/0120187 A1* | 8/2002 | Eiffert et al. .................. | 600/407 |
| 2002/0138302 A1 | 9/2002 | Bodnick ........................... | 705/2 |
| 2002/0143579 A1 | 10/2002 | Docherty et al. | |
| 2002/0143582 A1 | 10/2002 | Neuman et al. | |
| 2002/0165736 A1 | 11/2002 | Tolle et al. ....................... | 705/3 |
| 2003/0036683 A1 | 2/2003 | Kehr et al. | |
| 2003/0036923 A1 | 2/2003 | Waldon et al. | |
| 2003/0050799 A1 | 3/2003 | Jay et al. ......................... | 705/2 |
| 2003/0050802 A1 | 3/2003 | Jay et al. .......................... | 705/3 |
| 2003/0074225 A1 | 4/2003 | Borsand et al. .................. | 705/3 |
| 2003/0125985 A1* | 7/2003 | Rao et al. ......................... | 705/2 |
| 2003/0130873 A1 | 7/2003 | Nevin et al. ...................... | 705/3 |
| 2003/0135392 A1 | 7/2003 | Vrijens et al. .................... | 705/2 |
| 2003/0144884 A1 | 7/2003 | Mayaud | |
| 2003/0154109 A1 | 8/2003 | Martin et al. | |
| 2003/0158755 A1 | 8/2003 | Neuman | |
| 2003/0187690 A1 | 10/2003 | Miller et al. ...................... | 705/2 |
| 2003/0191667 A1 | 10/2003 | Fitzgerald et al. | |
| 2003/0236683 A1* | 12/2003 | Henderson et al. ............... | 705/2 |
| 2004/0002872 A1 | 1/2004 | Wright | |
| 2004/0006494 A1 | 1/2004 | Badinelli ......................... | 705/2 |
| 2004/0049407 A1 | 3/2004 | Rosenberg | |
| 2004/0059605 A1 | 3/2004 | Rubin et al. ..................... | 705/2 |
| 2004/0073454 A1 | 4/2004 | Urquhart et al. | |
| 2004/0078218 A1 | 4/2004 | Badinelli ......................... | 705/2 |
| 2004/0107120 A1 | 6/2004 | Melton, Jr. et al. ............... | 705/3 |
| 2004/0122702 A1 | 6/2004 | Sabol et al. | |
| 2004/0152959 A1 | 8/2004 | Williams et al. .............. | 600/300 |
| 2004/0172285 A1 | 9/2004 | Gibson | |
| 2005/0021368 A1 | 1/2005 | Burkeen et al. | |
| 2005/0027560 A1 | 2/2005 | Cook ............................... | 705/2 |
| 2005/0043965 A1 | 2/2005 | Heller et al. ...................... | 705/2 |
| 2005/0091083 A1 | 4/2005 | McGuigan et al. ............... | 705/3 |
| 2005/0119914 A1* | 6/2005 | Batch ............................... | 705/2 |
| 2005/0220862 A1 | 10/2005 | Bernstein | |
| 2005/0234740 A1* | 10/2005 | Krishnan et al. .................. | 705/2 |
| 2005/0251416 A1* | 11/2005 | Greene ............................. | 705/2 |
| 2006/0190323 A1 | 8/2006 | Olson et al. | |
| 2007/0214009 A1 | 9/2007 | Epstein et al. .................... | 705/2 |

OTHER PUBLICATIONS

"The Impact of Computerized Physician Order Entry on Medicaton Error Prevention" JAMIA 1999; 6:313-321.

"The Relationship Between Number of Medications and Weight Loss of Impaired Balance in Older Adults" JAGS 2004; 52:1719-1723.

*Product & Services*, Health Information Designs, Inc., originally found at http://www.hidinc.com/ext_prod.php3.

*Patient Education*, Health Information Designs, Inc., originally found at http://www.hidinc.com/ext_ped.php3.

*Prior Authorization*, Health Information Designs, Inc., originally found at http://www.hidinc.com/ext_pa.php3.

"*HID Releases Drug Explorer & Durbase II*", Health Information Designs, Inc., originally found at http://www.hidinc.com/ext_nws4.php3.

U.S. Appl. No. 11/458,054, filed Jul. 17, 2006, entitled "Compliance With a Medication Therapy Regimen".

U.S. Appl. No. 11/458,080, filed Jul. 17, 2006, entitled "Predictive Modeling and Risk Stratification of a Medication Therapy Regimen".

U.S. Appl. No. 11/458,071, filed Jul. 17, 2006, entitled "Health Risk Assessment of a Medication Therapy Regimen".

U.S. Appl. No. 11/458,066, filed Jul. 17, 2006, entitled "Identification of Inappropriate Medications in a Medication Therapy Regimen".

U.S. Appl. No. 11/458,059, filed Jul. 17, 2006, entitled "Optimization of a Medication Therapy Regimen".

Office Action for U.S. Appl. No. 11/458,054 dated Jul. 31, 2009.

Final Office Action for U.S. Appl. No. 11/458,054 dated Dec. 8, 2009.

Office Action for U.S. Appl. No. 11/458,054 dated Jun. 9, 2010.

Final Office Action for U.S. Appl. No. 11/458,054 dated Oct. 29, 2010.

Office Action for U.S. Appl. No. 11/458,059 dated Aug. 14, 2009.

Final Office Action for U.S. Appl. No. 11/458,059 dated Mar. 31, 2010.

Office Action for U.S. Appl. No. 11/458,066 dated Nov. 10, 2009.

Final Office Action for U.S. Appl. No. 11/458,066 dated Apr. 26, 2010.

Office Action for U.S. Appl. No. 11/458,066 dated Oct. 15, 2010.

Final Office Action for U.S. Appl. No. 11/458,066 dated May 12, 2011.

Office Action for U.S. Appl. No. 11/458,071 dated Feb. 2, 2010.

Final Office Action for U.S. Appl. No. 11/458,071 dated Aug. 18, 2010.

Office Action for U.S. Appl. No. 11/458,071 dated Jan. 6, 2011.

Office Action for U.S. Appl. No. 11/458,080 dated Sep. 15, 2009.

Final Office Action for U.S. Appl. No. 11/458,080 dated Jun. 8, 2010.

Office Action for U.S. Appl. No. 11/458,080 dated Jun. 21, 2011.

Office Action for U.S. Appl. No. 11/458,071 dated Sep. 14, 2012.

Office Action for U.S. Appl. No. 11/458,080 dated Oct. 12, 2012.

Final Office Action for U.S. Appl. No. 11/458,071 dated Sep. 7, 2011.

Office Action for U.S. Appl. No. 11/458,059 dated Aug. 4, 2011.

Final Office Action for U.S. Appl. No. 11/458,059 dated Feb. 16, 2012.

Final Office Action for U.S. Appl. No. 11/458,080 dated Jan. 31, 2012.

Final Office Action for U.S. Appl. No. 11/458,066 dated Jul. 3, 2012.

"Guidelines for Complete Safe and Accurate Discharge and Outpatient Prescription Writing", P&T News, Aug. 1995; vol. 16, 2B, 5 pages.

*Product & Services*, Health Information Designs, Inc., originally found at http://www.hidinc.com/ext_prod.php3, retrieved from the internet Sep. 21, 2003.

*Patient Education*, Health Information Designs, Inc., originally found at http://www.hidinc.com/ext_ped.php3, retrieved from the internet Nov. 3, 2003.

*Prior Authorization*, Health Information Designs, Inc., originally found at http://www.hidinc.com/ext_pa.php3, retrieved from the internet Nov. 3, 2003.

"*HID Releases Drug Explorer & Durbase II*", Health Information Designs, Inc., originally found at htto://www.hidinc.com/ext_nws4.php3, Sep. 1, 1998.

*Product & Services*, Health Information Designs, Inc., originally found at http://www.hidinc.com/ext_prod.php3, and obtained Jun. 15, 2006.

*Patient Education*, Health Information Designs, Inc., originally found at http://www.hidinc.com/ext_ped.php3, and obtained Jun. 15, 2006.

*Prior Authorization*, Health Information Designs, Inc., originally found at http://www.hidinc.com/ext_pa.php3, and obtained Jun. 15, 2006.

"*HID Releases Drug Explorer & Durbase II*", Health Information Designs, Inc., originally found at http://www.hidinc.com/ext_nws4.php3, Sep. 1, 1998.

Office Action for U.S. Application No. 11/458,071 dated May 22, 2013.

* cited by examiner

APPROPRIATENESS OF A MEDICATION THERAPY REGIMEN

TECHNICAL FIELD

The present disclosure relates generally to medication therapy management, and, more specifically, to determining the appropriateness a medication therapy regimen.

BACKGROUND

Patients on a medication therapy regimen may take multiple medications, have multiple medical providers and/or have multiple medical conditions. In many cases, medication information, medical provider information and medical condition information are of particular medical importance in managing a patient's medication therapy regimen. For example, drug-drug interactions may occur in patients taking multiple prescription drugs and are the result of one or more drugs interacting with, or interfering with, another drug or set of drugs, thereby resulting in, for example, decreased efficacy, toxicity, etc. Drug-disease interactions result when a medication intended for treatment of one disease is in conflict with the treatment of a different disease in the same patient. Avoiding drug conflicts, such as drug-drug, drug-illness and drug-age interactions, increases the safety and efficacy of prescription drugs. Duplication of a drug or class of drugs may result in an overdose. In other cases, failure to adhere to a medication therapy regimen may adversely affect the patient's health.

In addition to medical importance, medication information, medical provider information and medical condition information are important from an efficiency perspective. For example, duplication of a medication may result in an increased cost without any additional medical benefit, as well as a potential medical disadvantage. In some cases, medications may be replaced or combined by prescribing an alternative medication that has an improved medical effect and/or may also result in decreased cost to the patient.

However, medication information, medical provider information and medical condition information are often provided by disparate data sources. For example, a patient may have different medical providers for different medical conditions, resulting in different medication prescriptions. As a result, in many instances the patient, the patient's medical provider and/or the patient's pharmacist is not fully apprised of the patient's medication therapy regimen. A medical provider may therefore not be aware of a drug prescribed by another medical provider, and therefore may not be fully apprised of the potential medical effects, risks, alternatives and costs involved with the patient's medication therapy regimen. Further, a medical provider may not be aware of a patient's adherence to the medication therapy regimen and the patient may not fully appreciate the importance of adhering to the medical therapy regimen. Accordingly, such gaps in knowledge regarding a patient's medication therapy regimen thereby increases the risk of adverse health, decreased efficiency and increase cost. These risks may be further exacerbated by patient risk factors such as the patient's age, gender, ethnicity, weight, genetic predisposition, etc. For example, elderly patients have more complex medication therapy regimens with an increased importance placed on adhering to the medication therapy regimen.

DETAILED DESCRIPTION

Although the following text sets forth a detailed description of numerous different embodiments, it should be understood that the legal scope of the description is defined by the words of the claims set forth at the end of this patent. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term by limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

Figure 1:
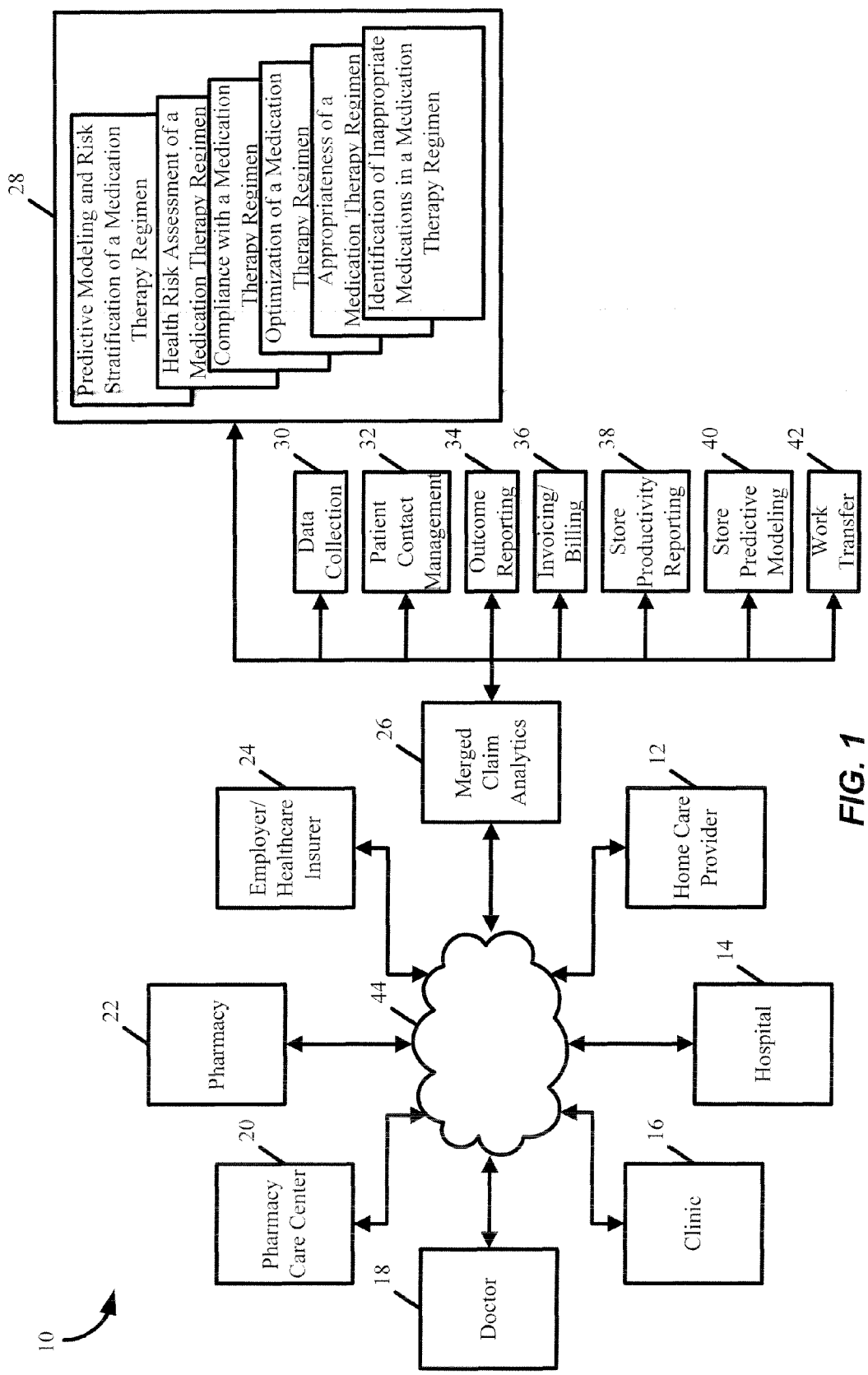
FIG. 1 is a block diagram of an embodiment of an intelligent network system for sharing medication information, medical information and medical provider information.

FIG. 1 is an exemplary schematic block diagram of an example of a data network and system 10 for providing medication therapy management. Referring to FIG. 1, the data network 10 may include medical providers, such as home care providers 12, hospitals 14, clinics 16 and doctors 18. Each of the medical providers may provide information relating to medications prescribed to the patient and medical conditions or ailments associated with an individual (hereinafter referred to as a "patient"). For example, home care providers 12 may provide medical condition and medication information for patient's receiving home medical care. Hospitals 14 and clinics 16 may provide medical condition and medication information resulting from medical aid administered to the patient during an emergency, scheduled visitation, operations, etc. Doctors 18 may provide medical information and medication information resulting from medical examinations.

The data network 10 may further include various pharmaceutical services, including pharmaceutical care centers 20 and pharmaceutical stores 22, which may provide medication information via prescriptions filled by the patient at the pharmacies. Additional pharmaceutical services provided by the pharmaceutical care centers 20 and pharmaceutical stores 22 may include doctors or pharmacists made available to the patient via electronic mail, telephone or the like, and which may provide medical and/or pharmaceutical advice to the patient, and, in turn make the results of such advice available to the data network 10. In still other cases, the pharmaceutical care centers 20 and pharmaceutical stores 22 may work in conjunction with doctors, hospitals and patient care centers to provide pharmaceutical services, including prescriptions and pharmaceutical advice. As explained further below, each of the pharmaceutical care centers 20 and pharmaceutical stores 22 may be provided with reimbursement codes relating to payments for services conducted in connection with the medication therapy management services, also described further below.

An employer and/or healthcare insurer 24 may be included in the data network 10 to provide information relating to insurance claims, including medical services, medical conditions and prescriptions claimed under a patient's insurance plan. The employer or insurer, referred to hereinafter as a "employer/healthcare insurer," may be, by way of example rather than limitation, a Managed Care Organization, an HMO, state Medicaid departments, a Medicare provider, a general insurer, employers of various sizes, or an aggregation of different sizes, so long as there exists a population of patients, whose medical expenses are, to some extent, covered by the employer/healthcare insurer 24.

Additionally, analytical services, such as a merged claim analytics database 26, may be included in the data network 10. The analytical services 26 may receive information from each of the medical providers 12, 14, 16, 18 and employer/healthcare insurers 24, including, but not limited to, medical condition and eligibility information, medical information and patient parameter information including name, contact information, patient risk factors such as age, ethnicity, weight, genetic predisposition, etc. In addition, the analytical services may include applications or systems 30 relating to data collection, storage and management to provide a centralized repository for the medical condition and eligibility information, medication information, patient parameter information or any additional patient information. For example, the analytical services 26 may be used to accumulate, analyze or download data relating to the operation of the pharmaceutical care centers 20, pharmaceutical stores 22, and more particularly to weighted data or prescriptions for medications. The analytical services 26 may periodically receive data from each of the pharmaceutical care centers 20 and pharmaceutical stores 22 pertaining to prescriptions filled by the individual patients.

Likewise, the analytical services 26 may accumulate, analyze and download data relating to medical and medication information from the employer/healthcare insurers 24, which may be provided as insurance claims data. For example, the analytical services 26 may receive information from the employer/healthcare insurer 24 related to medical claims of the healthcare insurer's patients. The medical claim data for each individual patient may be combined with the patient's medication data as compiled from various pharmaceutical stores 22 to create a complete medical and prescription file for each patient covered by the employer/healthcare insurer 24. In addition to the medication data complied from the pharmaceutical stores 22, the patient's file may be supplemented with data pertaining to prescriptions filled outside of the pharmaceutical stores 22 via the medical claim data provided by the employer/healthcare insurer 24.

Medical condition data relating to medical treatment or medical conditions, and medication data relating to medications prescribed by the medical provider to the patient may be provided from the medical providers 12, 14, 16, 18 and downloaded to the analytical services 26 for accumulation and analysis. As with data from the employer/healthcare insurer 24, medical condition data for each patient may be combined with the patient's medication data and medical claim data as compiled from various pharmaceutical care centers 20, pharmaceutical stores 22 and employer/healthcare insurers 24 to create a complete medical and prescription file for each patient associated with the medical provider. The patient file may thereby potentially include a complete, or near-complete, identification of the patient medication therapy regimen, including medical conditions, medications and information related thereto. The totality of this information, i.e., the patient's file, may be periodically transferred to and from the analytical services 26 and medical providers 12, 14, 16, 18, the pharmaceutical care centers 20, the pharmaceutical stores 22 and the employer/healthcare insurer 24 via the network 44. Further, the patients' files may be updated with additional data over the same network.

Further, the analytical services 26 may be operatively coupled to Retrospective Drug Use Review (RDUR) clinical Decision Support System (DSS) 28 which may conduct analyses using this information to provide and store additional information, including, but not limited to, results relating to predictive health risk modeling and risk stratification of a medication therapy regimen, health risk assessment of a medication therapy regimen, compliance with a medication therapy regimen, optimization of a medical therapy regimen, appropriateness of a medication therapy regimen, and identification of inappropriate medications in a medication therapy regimen. The results of such analyses may be used to manage the patient's medication therapy, and intervene in the patient's medication therapy as needed. The interventions or contacts with the patient may be managed by a patient contact management application or system 32. The outcomes of such management and interventions may be stored and managed by applications or systems 34 which may further report the outcomes to the medical providers 12, 14, 16, 18, the employer/healthcare insurers 24 and/or other pharmaceutical services.

In addition to analytical services, the merged claim analytics database 26 may include applications or be operatively coupled to systems 36 related to invoicing and billing for one or more of the above analytical services. Further, application or systems 38, 40, 42 may be provided relating to management of the pharmaceutical stores 22, including store productivity, store predictive modeling and work transfers.

Each of the home care providers 12, hospitals 14, clinics 16, doctors 18, pharmaceutical care centers 20, pharmaceutical stores 22, employer/healthcare insurers 24 and analytical services 26 are inter-operatively coupled via a network 44, which may comprise, for example, the Internet, a wide area network (WAN), or a local area network (LAN). The network 44 may be provided using a wide variety of techniques well known to those skilled in the art for the transfer of electronic data. For example, the network 44 may comprise dedicated access lines, plain, ordinary telephone lines, satellite links, combinations of these, etc. Additionally, the network 44 may include a plurality of network computers or server computers (not shown), each of which may be operatively interconnected in a known manner. Where the network 44 comprises the Internet, data communication may take place over the network 44 via an Internet communication protocol.

Although the data network 10 is shown to include one home care provider 12, hospital 14 clinic 16, doctor 18, pharmaceutical care center 20, pharmaceutical store 22, employer/healthcare insurer 24 and analytics database 26, it should be understood that different numbers of home care providers, hospitals, clinics, doctors, pharmaceutical care centers, pharmaceutical stores, employer/healthcare insurers and analytics databases may be utilized. For example, the data network 10 may include a plurality of home care providers 12, hospitals 14, clinics 16, doctors 18, pharmaceutical care centers 20, employer/healthcare insurer 24 and analytics databases 26, and hundreds or thousands of pharmaceutical stores 22, all of which may be interconnected via the network 44. According to the disclosed example, this configuration may provide several advantages, such as, for example, enabling near real time uploads and downloads of information, as well as periodic uploads and downloads of information. This provides for a primary backup of all the information generated in transactions where prescriptions are filled.

It should further be understood that each of the home care providers 12, hospitals 14, clinics 16, doctors 18, pharmaceutical care centers 20, pharmaceutical stores 22, employer/healthcare insurers 24 and analytics databases 26 may be coupled to the data network 10 by a network computer which may include a processor, a memory operatively coupled to the processor and/or a database operatively coupled to the processor and memory. In some instances, each home care provider 12, hospital 14, clinic 16, doctor 18, pharmaceutical care center 20, pharmaceutical store 22, employer/healthcare insurer 24 and analytics database 26 may maintain its own internal data network. The network computer may be a server computer of the type commonly employed in networking solutions.

Figure 2:
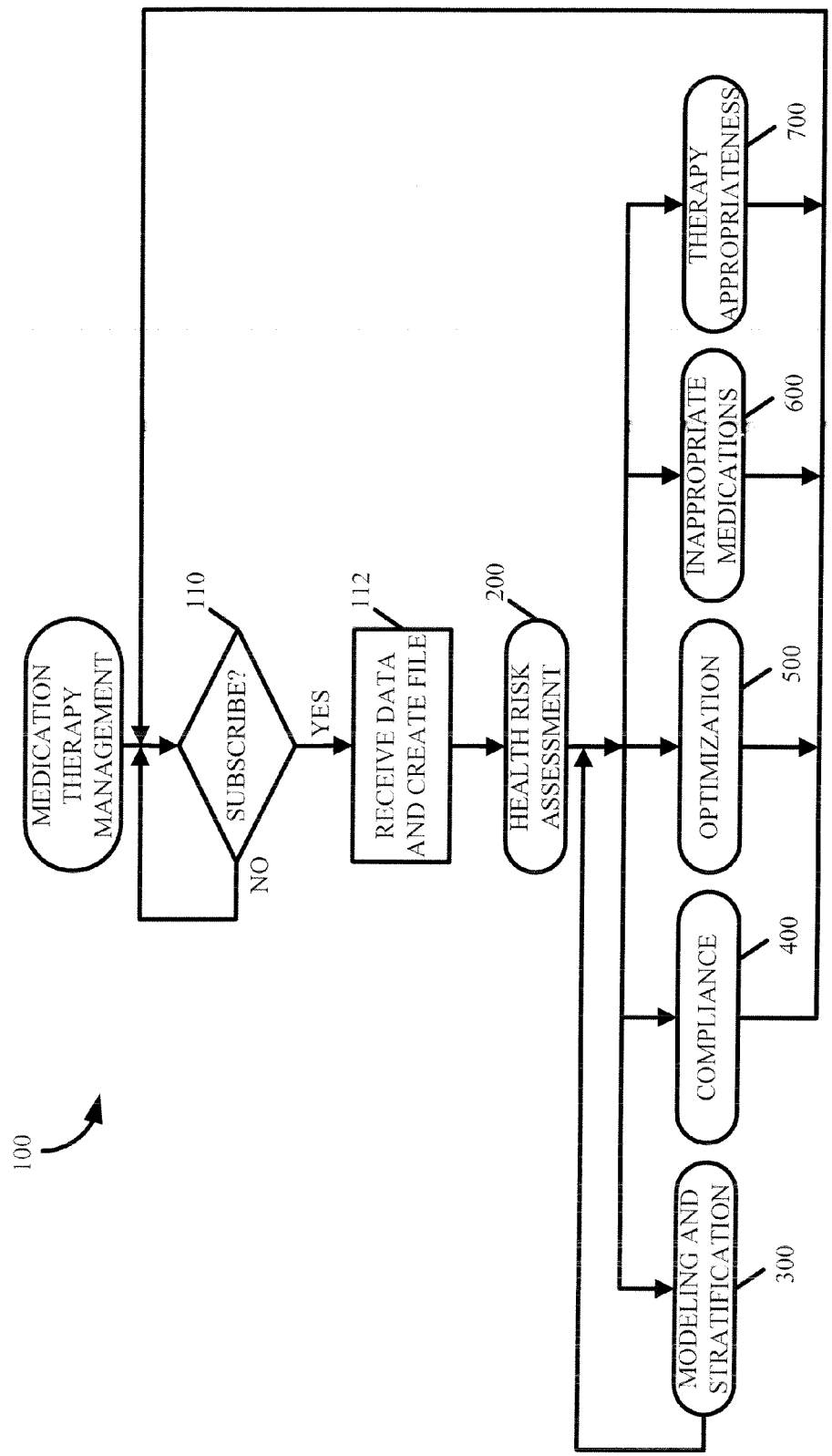
FIG. 2 is a flowchart of an embodiment of a medication therapy management routine.

FIG. 2 illustrates an example of a medication management routine 100 which may be executed within the data system 10 for managing the medication therapy regimen of one or more patients by improving communication between patients, medical providers and pharmacists. In turn, improved patient care may be provided from a safety, quality and cost perspective. In particular, the medication management routine 100 may be used to collect patient information, including, but not limited to, medical condition information, medication information and patient parameter information as provided above. The medication management routine 100 may further be used to assess health risks to a patient, to enhance patient adherence to a medication therapy regimen, to optimize a medication therapy regimen, identify inappropriate medications and assess the appropriateness of the medication therapy regimen, as well as identify and execute medication therapy interventions related to any of the above.

Beginning at block 110, the medication therapy management routine 100 determines whether a potential subscriber, such as an employer/healthcare insurer 24, a medical provider 12, 14, 16, 18 or pharmacy services 20, 22, wants to subscribe to the data network 10, and specifically to the medication therapy management service provided via the medication therapy management routine 100. Should the potential subscriber wish to subscribe to the medication therapy management service, the subscriber may provide current medical condition data and medication data for patients associated with the subscriber. If it is determined at block 110 that the potential subscriber does not wish to subscribe to the medication therapy management service, then control reverts back to await another potential subscriber. Alternatively, the subscriber may wish to subscribe temporarily or permanently to the medication therapy management service.

If the potential subscriber subscribes to the medication therapy management service, as illustrated in block 110, the medication therapy management routine 100 will request that the subscriber provide all current medication data and medical condition data for each individual patient, or at least of those patients to whom the subscriber wishes to apply the medication therapy management service. Medication prescription data for each individual may also be obtained from multiple, related pharmaceutical stores 22, and medical claims data may be received from employer/healthcare insurers 24. Medication data from multiple sources may result in the merging of the data to provide as complete a medication record as possible without overlap. For example, medication prescription data from the pharmaceutical stores 22 may be merged with the medical claims data from the employer/healthcare insurers 24, and the merged data may be provided as the medication data. Such data may be transmitted through the network 10.

At block 112, the medication therapy management routine 100 may receive patient information from the subscriber for all patients associated with the subscriber, including, but not limited to, patient parameter data (e.g., name, contact information, patient risk factors, etc.), medical condition data relating to a medical condition or ailment of the patient, and medication data relating to medications prescribed or administered to the patient. The patient risk factors in patient parameter data may include, but are not limited to, age, weight, ethnicity, genetic predisposition or any other factors that may be taken into account in assessing risk. As previously indicated, the data may be provided as medication data from a pharmaceutical store 22, as medical visit reports from medical providers and/or medical claims data from employer/healthcare insurers 24. In addition, subscriber information regarding the subscriber may be provided, such as the subscriber's name and contact information. Data from the subscriber may be continually or periodically obtain to update existing patient information and to include information on newly enrolled patients.

Although the medication therapy management services may be provided to any patient, the medication therapy management services may provide more accurate outcomes by initially identifying those patients that may benefit the most from such services and restricting the field to those patients. As such, the medication therapy management routine 100 may receive eligibility data from the pharmaceutical store 22, medical providers 12, 14, 16, 18, 20 and/or employer/healthcare insurers 24, or extrapolate the eligibility data from among the data mentioned above. For example, the eligibility data may be derived from the patient parameter data such that only patient of a certain age are eligible for the medication therapy management services. Of course, the eligibility data may be defined along any one factor or combination of factors, such as patient risk factors. Eligibility data may also be based upon insurance plans, such that only patients within a particular insurance plan or type of insurance plan (e.g., Medicare) are eligible for the medication therapy management services.

As shown in block 112, where the subscriber provides the requested data, a complete patient file is created for each patient based on the medical condition and medication data supplied by the subscriber combined with any additional medication data accessible from the related pharmaceutical stores 22. If current data on one or more patients is not available at the time of subscription, the medication therapy management services may proceed based on all future medication data and medical condition date which may be continually or periodically provided by the subscriber. The subscriber may update the medical condition data and the medication data in a variety of ways. For example, the subscriber may provide the updates periodically, in real time, or in near-real time.

Patient files may be created for each patient upon receipt of the medical condition data and the medication data from the subscriber. Alternatively, where patients have previously had prescriptions filled at the pharmaceutical stores 22, individual patient files may already exist. In this case, the patient files could simply be supplemented with any additional medical condition data and medication data obtained from the subscriber. Individual patients may have existing unique customer ID numbers that may be stored. The unique customer ID may be associated with a large amount of personal information relating to the patient. For example, the analytics database 26 may store information including the patient's name, address, electronic address, telephone number, birth date, social security number, employer/healthcare insurers 24, etc. Also associated with the customer ID may be the patient's electronic file containing the medical condition data and medication data as collected from the subscriber and from the various pharmaceutical stores 22. The patient's personal information, the medical condition data and medication data, may be protected using appropriate security methods, linked to the patient's unique customer ID, and stored in a customer account database using methods well known to those of ordinary skill in the art.

Communication may be established with the patient upon creating a patient file containing the patient's medical condition data and medication data, or otherwise receiving the patient's medical condition data and medication data. In one example, a series of letters and forms may be generated for the patient and the patient's medical provider. The patient may receive an initial letter, or other form of communication, offering and explaining the medication therapy management services available to the patient and providing the unique customer ID. The letter may further explain how a participating pharmacist may review all of the patient's medications and the benefits provided therewith, such as simplifying the patient's medication schedule, ensuring the patient receives the most beneficial treatments available and verifying the medications are safe and effective for the patient and the patient's health conditions. The letter may invite the patient to enroll in the medication therapy management services by calling a toll-free number, for example, and provide an explanation of the enrollment process. For example, during enrollment, a care provider may request the patient's unique customer ID provided with the communication, request the patient's local pharmacist's contact information, provide an explanation of the services and conduct a brief review of the patient's medication therapy regimen. In addition, the letter may explain that the patient may undergo an initial interview via telephone, or other form of communication, and/or schedule an appointment with a local participating pharmacist, during which the participating pharmacist reviews all of the patient's medications, answers any of the patient's questions, provides a complete list of the patient's current medications from all of the patient's medical providers, and provides a dosing calendar which tells the patient when to take the medications and which the patient may provide to the medical provider during medial visits such that the medical provider will know exactly which medications the patient is taking.

In addition to communicating with the patient, communication may be established with the patient's medical provider(s), which may be provided as a letter following the telephone and or pharmacist interviews with the patient. The letter to the medical provider may include information about the patient (e.g., name, date of birth, etc.) along with a medication profile developed from interviewing the patient. The medication profile may summarize the patient's current/recent medication therapy regimen. The letter may further request the medical provider to review the medication profile in order to determine if the patient medication therapy regimen is in accordance with the medial provider's records and in order to provider medical assessments regarding the patient's medical therapy regimen. For example, given the medication profile and the patient's medical information as maintained by the medical provider, the medical provider may assess drug/drug interactions, drug/disease interactions, duplicate therapies, adherence to a medication therapy, medications that may be discontinued, or any other professional medical assessment. The letter may further invite the medical provider to initiate an optimization review of the patient's medication therapy regimen, an example of which is provided below with reference to FIG. 6.

As mentioned, medical condition data and medication data may be continually provided from a subscriber. The medication therapy management routine 100 may update the patient file with the latest medical condition data and medication data from the subscribers. For example, a network computer at each pharmaceutical store 22 may periodically transfer medication data to the analytics database 26. Likewise, medical claim updates can be transferred from the employer/healthcare insurers 24 and information resulting from medical visits may be transferred from the medical providers. Analysis of each patient's file proceeds based on the combined medical condition data and medication data as obtained from the employer/healthcare insurers 24, pharmaceutical stores 22 and medical providers 12, 14, 16, 18. Users, such as pharmacist, may access a patient's file on the customer account database through the web portal provide via the website by accessing a communication device such as a computer at the pharmaceutical store 22. The pharmacist may further enter any new medication data as provided from prescriptions into the patient's file. This information may be transmitted through the network data 10 to the analytics database 26 via a data collection service or routine 30.

At block 200, the medication therapy management routine 100 executes an initial health risk assessment routine 200 for each patient to assist in risk stratification of patients for select interventions. In particular, the health risk assessment routine 200 evaluates the medical condition information and medication information to initially determine any potential adverse health outcomes associated with the patient, determine the likelihood of such adverse health outcomes and provide the patient and/or medical provider with the results. The health risk assessment routine 200 may further account for one or more patient risk factors of the patient, including, but not limited to, age, ethnicity, gender, genetic predisposition and weight. For example, because medication therapy management is of particular importance with elderly patients, the health risk assessment routine 200 may further account for the age of the patient. Generally, when a patient first enrolls, the medication therapy management routine 100 may not have any previous patient information to rely on as a source of medical condition information and medication information, such as insurance claims history data from an employer/healthcare insurer 24. Accordingly, the health risk assessment routine 200 may be executed whenever a patient initially enrolls in the medication therapy management, enrolls in a healthcare insurance plan via an employer/healthcare insurer 24, first contacts a medical provider 12, 14, 16, 18 or first fulfills a prescription from a pharmaceutical store 22. The health risk assessment routine 200 may be executed for all existing patients associated with an employer/healthcare insurer 24 or a medical provider 12, 14, 16, 18 when the employer/healthcare insurer 24 or medical provider 12, 14, 16, 18 first subscribes to the data network 10 and the medication therapy management service.

Following the health risk assessment at block 200, the medication management routine 100 may execute one or more routines for managing the patient's medication therapy regimen, including a modeling and stratification routine 300, a medication therapy regimen compliance routine 400, a medication therapy regimen optimization routine 500, an inappropriate medications routine 600 and a medication therapy regimen appropriateness routine 700. Each of the routines 200, 300, 400, 500, 600, 700 may be performed continually or periodically in order to actively manage each patient's medication therapy regimen.

The modeling and stratification routine 300 may be used to identify patients that will most benefit from medication therapy management interventions, and to what degree such interventions should be executed. In particular, the modeling and stratification routine 300 evaluates medical condition information and medication information to identify any identified, potentially adverse health outcomes. The modeling and stratification routine 300 may further evaluation the likelihood of the adverse health outcome and identify intervention opportunities accordingly. Generally, a patient will have already undergone enrollment and/or has a healthcare insurance claim history from which the modeling and stratification routine 300 may base its analysis. The modeling and stratification routine 300 may be used with respect to all patients whose information is maintained by the medication therapy management routine 100, or for those patients associated with a particular medical provider and/or employer/healthcare insurer 24. Results from the modeling and stratification routine 300 may be provided to the other routines 400, 500, 600, 700 for further management of the patient's medication therapy regimen.

The medication therapy regimen compliance routine 400 may be used to improve patient adherence to the medication therapy regimen prescribed by the patient's medical provider. In particular, the medication therapy regimen compliance routine 400 identifies those patients that are new to a medication therapy regimen, those patients that have not refilled or reordered a prescription, or that have been predicted as likely being noncompliant to the medication therapy regimen based on past performance (e.g., failure to refill or reorder a prescription). The medication therapy regimen compliance routine 400 may then be used to contact or otherwise intervene in the patient's medication therapy regimen to provide consultation to the patient regarding adherence to the medication therapy regimen.

The medication therapy regimen optimization routine 500 may be used to optimize a patient's medication therapy regimen by analyzing the medication therapy regimen, identifying opportunities for optimization and modifying the medication therapy regimen to eliminate duplicative medications, reduce the number of medications, reduce the cost to the patient, improve the medical effect of the medication and/or reduce a side effect. The medication therapy regimen optimization routine 500 may be particularly useful for elderly patients having multiple medications, multiple medical conditions and/or multiple medical providers.

The inappropriate medications routine 600 may be used to identify inappropriate medications in a patient's medication therapy regimen, and, in particular, identify inappropriate medications in an elderly patient's medication regimen given medical conditions associated with the elderly patient. Identification of inappropriate medications may assist in preventing potentially adverse health effects or unintended consequences in the patient by preventing dispensation of such medications. As such, the inappropriate medications routine 600 may evaluate elderly patient's medical condition information and medication information to identify any potentially adverse health outcomes, and interventions in the person's medication therapy regimen to prevent the adverse health outcome. Modifications to the medication therapy regimen may then be conducted, such as removing or replacing the medication that would have potentially caused the adverse health outcome.

The medication therapy regimen appropriateness routine 700 may be used to identify patients that may be receiving sub-optimal care based on established standards of care. For example, national guidelines have been established for treating particular chronic illnesses. The medication therapy regimen appropriateness routine 700 may evaluate a patient's existing medication therapy regimen for patients having a particular medical condition, or in some cases identify patients that are not on any medication therapy regimen. The medication therapy regimen appropriateness routine 700 compares the medication therapy regimen with data relating to treatment guidelines and determines a level of compliance between the two. Intervention in the patient's medication therapy regimen may be conducted for those instances where the medication therapy regimen did not comply with the established standard of care.

Although the medication management routine 100, including the routines, 200, 300, 400, 500, 600, 700, may be provided using various implementations, in one example the medication management routine 100 is provided as a distributed routine that may be carried out across the data network 10 by one or more of the medical providers 12, 14, 16, 18, 20, employer/healthcare insurers 24, pharmaceutical stores 22 and pharmaceutical services 26. As such, the medication therapy management routine 100 may be carried out via the Internet wherein each of the medical providers 12, 14, 16, 18, employer/healthcare insurers 24, pharmaceutical stores 22 and pharmaceutical care centers 20 may conduct their respective portion of the routine 100 and share their information, analyses, results, etc. via an Internet portal, such as a secured website. In another instance, core services associated with the medication therapy management routine 100, such as receiving and evaluating medical condition information and medication information may be conducted within a centralized database or network of computers such as the analytics services 26, whereas other functions, such as intervening in a patient's medication therapy regimen, may be conducted with the assistance of the medical providers 12, 14, 16, 18, the pharmaceutical care centers 20, the pharmaceutical stores 22 and/or the employer/healthcare insurers 24.

Figure 3:
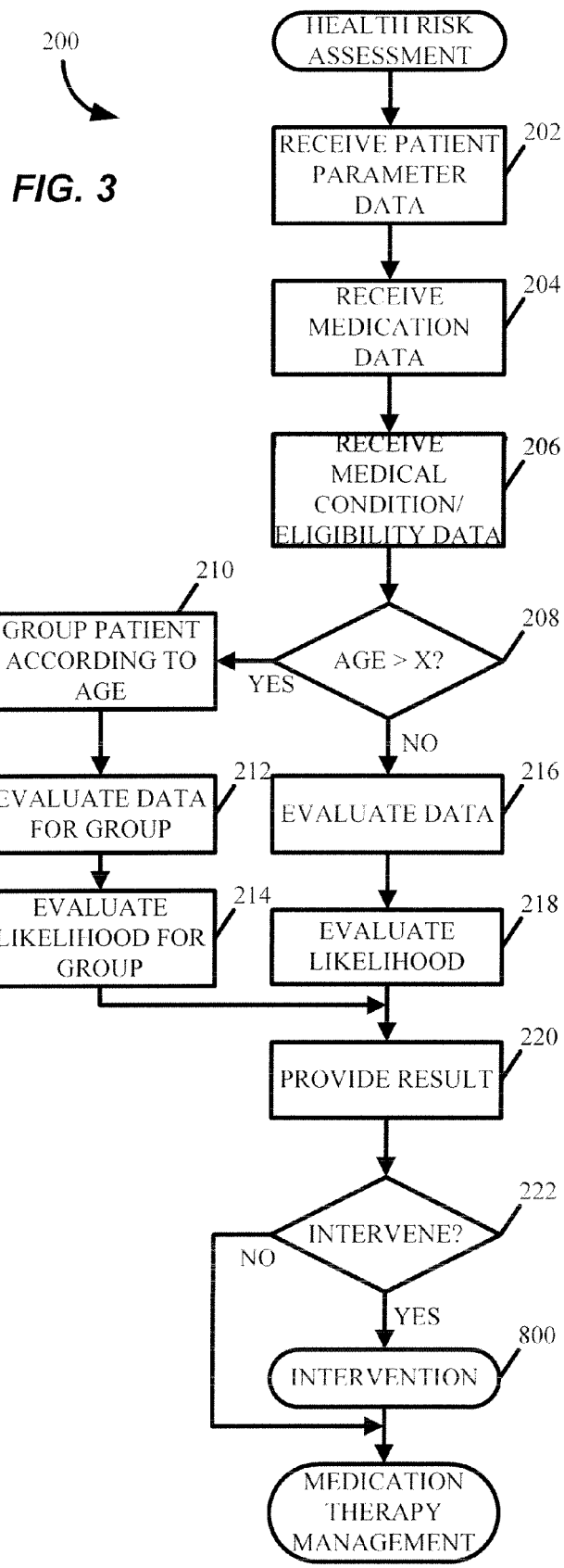
FIG. 3 is a flowchart of an embodiment of a health risk assessment routine for assessing an adverse health outcome associated with a medication therapy regimen.

FIG. 3 illustrates an example of a health risk assessment routine 200 shown schematically in FIG. 2. As previously indicated, the health risk assessment routine 200 may be executed for each new patient to the medication therapy management services as an initial health risk evaluation. The health risk assessment routine 200 may be executed on an event basis, such as for each new subscriber or newly-enrolled patient, on a continual basis or on a periodic basis such as once a year. The health risk assessment routine 200 may be executed by the analytics database 26, and more specifically by a merged claims analytics database 26 and/or a Retrospective Drug Use Review (RDUR) client decision support system 28 associated with the merged claims analytics database 26.

Beginning at block 202, the routine 200 receives patient parameter data, including, but not limited to, the patient's name, contact information (e.g., address, electronic address, telephone number, etc.), age data (e.g., age and/or birth date), medical provider(s), etc. The patient parameter data may further include patient risk factor data which may be used to assess a health risk of the patient. The patient risk factor data may include, but is not limited to, age, ethnicity, gender, genetic predisposition and weight. At block 204, the routine 200 receives medication data relating to one or more medications being used by the patient, and at block 206, the routine 200 receives medical condition data relating to one or more medical conditions such as drug inferred diseased states, medical claims data and/or medical history or diagnoses associated with the patient. Examples of the medication data that may be utilized by the health risk assessment routine 200 include, but are not limited to, the name of the medication, potential side effects, potential interactions with other medications, medical conditions the medication is meant to address, the patient's duration of use and the patient's utilization of a medication such as a rate or amount of use, rate or amount of refills, medication dosage, etc. In addition to receiving medical condition data at block 206, the routine 200 may receive eligibility data to verify or determine whether the patient is eligible for the service.

Generally, the data received at blocks 202, 204, 206 may be received by retrieving the patient file created at block 112 of the medication therapy management routine 100. Alternatively or in addition, some or all of the data received at blocks 202, 204, 206 may be received as part of a data transfer from a new subscriber to the medication therapy management service, as provided at block 112 of the medication therapy management routine 100. For example, an employer/healthcare insurer 24 may provide data on all persons insured by the employer/healthcare insurer 24 when the employer/healthcare insurer 24 subscribes to the medication therapy management services at blocks 110, 112. Likewise, a medical provider may provide such data on all persons that are patients of the medical provider 12, 14, 16, 18, and a pharmaceutical store 22 may provide such data as a result of all prescriptions fulfilled by persons at the store. In some cases, the data may be provided from different sources, such as the medical condition data from different medical providers and the medication data from different pharmaceutical stores 22.

In another example, whenever a patient first enrolls in an insurance plan with an employer/healthcare insurer 24, first fulfills a prescription with a pharmaceutical store 22 and/or first visits a medical provider, the patient may provide the data via a handwritten form which may then be entered into the analytics database 26 or the patient may provide the data through a website. If a patient file already exists for the patient, this data may be used to update the patient file.

As previously mentioned, the health risk assessment routine 200 may be particularly relevant for patients having particular patient risk factors. For example, the health risk assessment routine 200 may be particularly relevant for elderly patients who may be prescribed several different medications and/or have several medication conditions which may increase the risk for adverse health outcomes. Further, elderly patients may have unique medical needs that need to be addressed. Accordingly, at block 208 the health risk assessment routine 200 may determine whether or not the patient's age exceeds a predetermined threshold, in which case the patient is identified as an elderly patient and grouped accordingly at block 210. In one example, the identified elderly patients may be further grouped according to age (e.g., 80-84, 85-90, etc.). However, it is noted that other patient risk factors may be accounted for at block 208.

For each identified elderly patient, the health risk assessment routine 200 evaluates the medical condition data and the medication data at block 212 to identify potentially adverse health outcomes. In one example, the evaluation may include determining potential interactions between various medications being used by the patient, and interactions between a medication and a medical condition. In addition, the evaluation may identify instances of over-utilization which may indicate abuse of the medication which may lead to an overdose or instances of underuitilization (i.e., lack of compliance with a medication therapy regimen) which may exacerbate the medical condition the medication is meant to address. The evaluation may also identify medications which may no longer be required due to duplication of the same or similar medications, or because the medical condition for which the medication was prescribed no longer exists. In some instances, the evaluation may identify instances of fraud. In each instance where a potentially adverse health outcome is identified, the severity of the identified adverse health outcome (e.g., slight discomfort, mental debilitation, significant discomfort, death, etc.) may be determined.

Upon identifying and evaluating potentially adverse health outcomes resulting from the medical conditions and/or medication data, the health risk assessment routine 200 determines the likelihood that such an identified adverse health outcome would occur at block 214. The determination of the likelihood of the identified adverse health outcome occurring, such as a degree of risk, may be based on one or a combination of a number of factors related to the patient's medication therapy regimen, including for example: number of medications, therapeutic classes of medications, number of pharmacies, number of doctors, inferred disease(s), actual disease(s), age and gender of patient, and laboratory data if provided.

While not necessarily required, the health risk assessment routine 200 may automatically develop a health risk index or medication therapy index which indicates the degree to which the identified adverse health outcome may occur based on the above factors. Specifically, a system comprising software specially designed for such analysis may be used to assign patients their appropriate health risk index or medication therapy index score. The software may be accessible via the data network 10. Hence, the employer/healthcare insurer 24, the pharmaceutical stores 22, the medical providers and other authorized users, including the patient, may have access to, or otherwise be provided with, the results of the evaluation at block 220. The results may include the identified, potentially adverse health outcomes, the severity of each identified, potentially adverse health outcome and the likelihood of each identified, potentially adverse health outcome. Further, the results may include the causes of such identified, potentially adverse health outcomes and potential solutions (e.g., replacing a medication, adherence to a medication therapy regimen) or recommendations (e.g., consult medical provider).

Referring back to block 208, if the patient is not identified as an elderly patient as determined at block 208, the patient's medical condition data and medication data may still be evaluated for potentially adverse health outcomes, similar to block 212, though the results, such as the potential health outcome and the severity thereof, may be different due to the patient's age. Further, the likelihood of the identified adverse health outcome occurring is determined at block 218, which may be accomplished by developing a health risk index or medication therapy index as at block 214. Again, the age of the patient may result in a different likelihood of occurrence than at block 214, even if the identified, potentially adverse health outcomes would otherwise be similar. The result of the evaluations is provided at block 220.

Based on the results provided at block 220, and in particular, based on the likelihood and severity of any identified, potentially adverse health outcome, the health assessment routine 200 determines whether an active intervention is necessary at block 222. For example, if an identified, potentially adverse health outcome has a 10% chance of resulting in permanent harm to the patient, the routine 200 may determine that an intervention in the patient's medication therapy regimen is necessary, which is conducted using an intervention routine 800. On the other hand, if an identified, potentially adverse health outcome has only a 2% chance of resulting in slight discomfort to the patient, intervention may not be required. As will be described further below, intervention in a patient's medication regimen may include contacting the patient and/or the patient's medical provider, determining the appropriate level of contact, such as calling the patient immediately or consulting the patient the next time the patient refills a prescription, etc. A recipient of the results information, such as a pharmacist, may be prompted to conduct the appropriate intervention. If an intervention is not necessary, or after the invention has been initiated, control may return to the medication therapy management routine 100.

Figure 4:
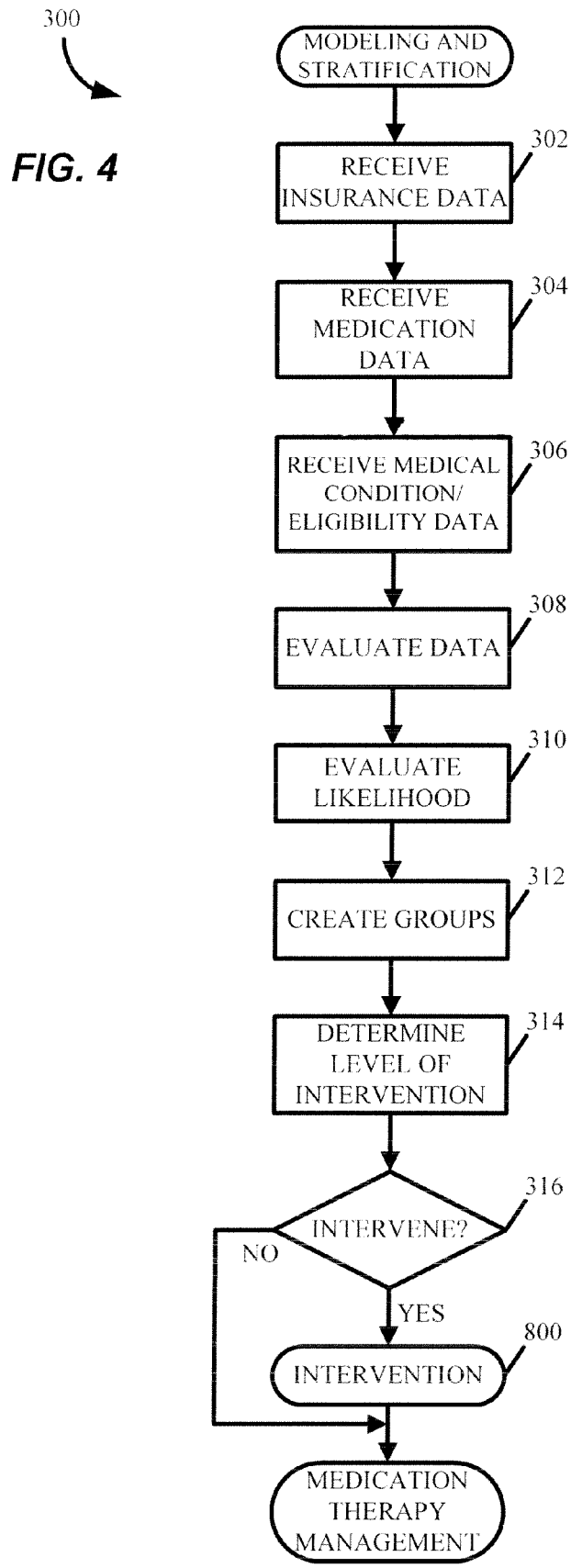
FIG. 4 is a flowchart of an embodiment of a modeling and stratification routine to assess an adverse health outcome associated with the medication therapy regimen.

FIG. 4 illustrates an example of a modeling and stratification routine 300 shown schematically in FIG. 2. As previously indicated, the modeling and stratification routine 300 may be used to identify those patients that will most benefit from medication therapy management intervention, and to what degree such interventions should be executed. In particular, the modeling and stratification routine 300 may be executed by the analytics database 26, and more specifically by a merged claims analytics database 26 and/or a Retrospective Drug Use Review (RDUR) client decision support system (e.g., applications or systems 30, 32 for patient health risk assessments, predictive health risk modeling and stratification).

Although many aspects of the modeling and risk stratification routine 300 may be similar to the health risk assessment routine 200, the health risk assessment routine 200 may be conducted as an initial assessment of health risks to the patient without the benefit of healthcare insurance claims data, such as medical claims data and medication claims data. Instead, the health risk assessment routine 200 may be primarily dependent on data provided from the patient. The modeling and risk stratification routine 300, on the other hand, may use insurance claims data provided from the employer/healthcare insurer 24 to identify those patients that could benefit from intervention based on an identified, potentially adverse health outcome.

Beginning at block 302, the modeling and risk stratification routine 300 receives insurance data relating to medical and medication (e.g., prescription) insurance claims made by the patient. At block 304, the routine 300 receives medication data relating to one or more medications being used by the patient, and at block 306, the routine 300 receives medical condition data relating to one or more medical conditions such as drug inferred diseased states, medical claims data and/or medical history or diagnoses associated with the patient. Examples of the medication data that may be utilized by the modeling and risk stratification routine 300 include, but are not limited to, the name of the medication, potential side effects, potential interactions with other medications, medical conditions the medication is meant to address, the patient's duration of use and the patient's utilization of a medication such as a rate or amount of use, rate or amount of refills, medication dosage, etc. In addition to receiving medical condition data at block 306, the routine 300 may receive eligibility data to verify or determine whether the patient is eligible for the service.

Generally, the data received at blocks 302, 304, 306 may be received by retrieving the patient file created at block 112 of the medication therapy management routine 100. Alternatively or in addition, some or all of the data received at blocks 302, 304, 306 may be received as part of a data transfer from an employer/healthcare insurer 24 which may provide data on all persons insured by the employer/healthcare insurer 24 when the employer/healthcare insurer 24 subscribes to the medication therapy management services and provides updates to the patient file. The medication data may also be received from a pharmaceutical store 22 whenever the associated prescription is covered in all or in part by the employer/healthcare insurer 24, and the medical condition data may be received from a medical provider whenever the associated medical exam and treatment is covered by the employer/healthcare insurer 24.

At block 308, the modeling and risk stratification routine 300 evaluates the medical condition data and the medication data to identify potentially adverse health outcomes. As with the health risk assessment routine 200, the evaluation may include determining potential interactions between various medications being used by the patient, and interactions between a medication and a medical condition. The evaluation at block 308 may also identify instances of over-utilization or underutilization, identify medications which may no longer be required or are duplicative. In each instance where a potentially adverse health outcome is identified, the severity of the identified adverse health outcome may be determined.

Upon evaluating identified, potentially adverse health outcomes resulting from the medical conditions and/or medication data, the modeling and risk stratification routine 300 determines the likelihood that such an adverse health outcome would occur at block 310, which may be based on one or more factors related to the patient's medication therapy regimen, including the number of medications, therapeutic classes of medications, number of pharmacies, number of doctors, inferred disease(s), actual disease(s), age and gender of patient, and laboratory data. The modeling and risk stratification routine may develop a health risk index or medication therapy index which indicates the degree to which the adverse health outcome may occur based on the above factors.

Based on the likelihood the identified, potentially adverse health outcome occurring, the routine 300 create groups at block 312. Each of the groups may be determined based on patients having the same or range of severity in identified, potentially adverse health outcomes. Alternatively or in addition, the groups may be based on patients having the same likelihood or range of likelihood of having an identified, potentially adverse health outcome occur. For example, those patients having a severe potential health outcome (e.g., disablement or death) and an appreciable risk of such an outcome occurring (e.g., greater than 10%) may be grouped accordingly, whereas other patients having a less severe potential health outcome (e.g., slight discomfort) with a high risk of such an outcome occurring (e.g., greater than 50%) may be provided in another group.

Based on the degree of severity of the identified, potentially adverse health outcome and the likelihood of such an outcome occurring, the modeling and risk stratification routine 300 creates an intervention severity index at block 314. The intervention severity index is representative of the level of urgency involved in intervening in the patient's medication therapy regimen, and the modeling and risk stratification routine 300 associates each group with a particular intervention level. In addition to being defined by the intervention severity index, the intervention levels may be defined by the level or methodology of contact (e.g., during a prescription refill, by telephone) and who to contact. Accordingly, a high intervention severity index may be associated with a intervention level that results in contacting the patient and the patient's physician by telephone, electronic mail or other immediate and direct forms of communication. On the other hand, a low intervention severity index may be associated with an intervention level where a pharmacist will consult the patient when the patient next refills a prescription.

Based on the level of intervention determined at block 314, the modeling and risk stratification routine 300 determines whether an intervention is necessary at block 316. If so, the routine 300 may conduct the intervention in accordance with the determined level of intervention using the intervention routine 800. Otherwise, if intervention is not necessary, control may return to the medication therapy management routine 100.

Figure 5:
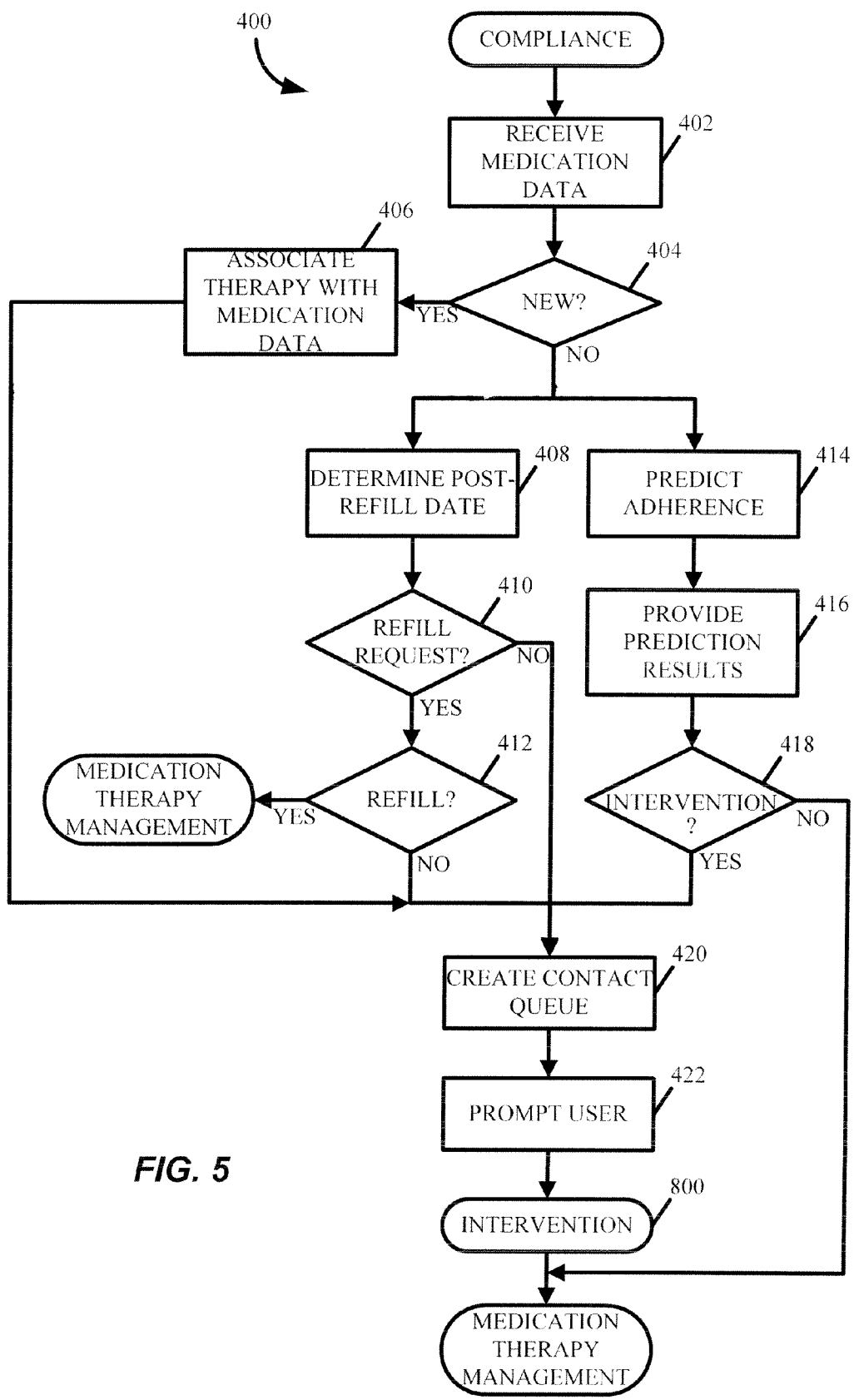
FIG. 5 is a flowchart of an embodiment of a medication therapy regimen compliance routine to determine compliance with the medication therapy regimen.

FIG. 5 illustrates an example of a medication therapy regimen compliance routine 400 shown schematically in FIG. 2. As previously indicated, the medication therapy regimen compliance routine 400 may be used to improve patient adherence to the patient's medication therapy regimen. In one example, the medication therapy regimen compliance routine 400 may be used for those patients that have been identified from the modeling and risk stratification routine 300 as underutilizing their medication therapy regimen which may indicate noncompliance with the medication therapy regimen, such as regularly taking a medication and/or regularly refilling or reordering a prescription. Accordingly, the medication therapy regimen compliance routine 400 may be used to determine whether intervention is required and/or to identify those patients that require intervention. The medication therapy regimen compliance routine 400 may be particularly useful for those patients taking an oral medication for diabetes; medications for cholesterol such as statins, fibrates, niacin and combinations thereof; medications for hypertension such as beta blockers, Ace-I inhibitor and Angiotensin II receptor blockers; medications for thyroid; medications for osteoporosis; medications for depression; medications for benign prostatic hypertrophy (BPH); and medications for Parkinson's disease. However, it is noted that the above list is not limited thereto, but is provided as examples of various medicals conditions for which the routine 400 may be useful. Accordingly, the medication therapy regimen compliance routine 400 may extend to other medical conditions beyond those listed above. Although the medication therapy regimen compliance routine 400 may be executed across the data network 10, in one example, the medication therapy regimen compliance routine 400 is executed by a Retrospective Drug Use Review (RDUR) clinical Decision Support System (DSS) operatively coupled to the analytics database 26.

Beginning at block 402, the medication therapy regimen compliance routine 400 receives medication data relating to one or more medications being taken by the patient. Examples of the medication data that may be utilized by the medication therapy regimen compliance routine 500 include, but are not limited to, the name of the medication, prescriptions for the medication, refills dates for refilling the prescription, the name and contact information of the person (e.g., medical provider) that prescribed the medication, medical conditions the medication is meant to address, the patient's duration of use and the patient's utilization of a medication such as a rate or amount of use, rate or amount of refills, medication dosage, etc. The medication data may further include prescription history data which may include previous refill dates on the same or other medications, dates the prescriptions refills were requested, dates the prescription refills were fulfilled (e.g., picked up by the patient) and other trending data. The prescription history data may be based upon information provided by the patient and contained within a Patient Medication Record described further below in connection with the medication therapy regimen optimization routine 500.

Generally, the data received at block 402 may be received by retrieving the patient file created at block 112 of the medication therapy management routine 100. Alternatively or in addition, some or all of the data received at block 402 may be received as medication insurance data from an employer/healthcare insurer 24, from a pharmaceutical store 22 or network which may maintain data on all prescriptions fulfilled by the pharmaceutical stores 22, and from a medical provider which may provide data on medications prescribed by the medical provider.

Because patients, and specifically elderly patients, may be new to a particular medication therapy regimen which may include a new medication to an existing medication therapy regimen, the patient may not be fully apprised of the importance of regularly taking the medication and refilling the medication. Failure to do so could lead to significantly adverse health effects. Accordingly, at block 404, the medication therapy regimen compliance routine 400 determines whether the patient is new to a particular medication therapy regimen. If so, the routine 400 associates the new medication therapy regimen with one or more prescriptions at block 406, which may include updating the analytics database 26 with the addition data. Following block 406, an intervention into the patient's medication therapy regimen is established, as described further below.

If the patient is not new to the medication therapy regimen, the medication therapy regimen compliance routine 400 may determine compliance with respect to existing patients and existing medication therapy regimens. For example, at block 408 the routine 400 may determine a post-refill date, which may be a predetermined number of days or range of days following a refill date associated with the prescription. For example, a prescription with a refill date of January 1 may result in a post-refill date of January 8, or a range of January 8-10 if a range of days is chosen. As such, the post-refill date allows for a "grace period" for patients to order a refill and/or execute a refill of the prescription. The post-refill date may depend on the importance of the medication, and in some cases the post-refill date may be set to 1 day or 0 days, thereby causing an intervention to be triggered if the patient fails to request (e.g., re-order) or fulfill the prescription by the refill date.

Once the post-refill date is determined, the routine 400 determines whether or not the patient has requested a refill of the prescription by the post-refill date. As is known, a patient may request a refill for a prescription by contacting a pharmaceutical store 22, which may be via electronic mail, telephone, a request through a website, etc. The routine 400 receives the refill request, and the request and the date thereof maybe stored in the analytics database 26. If the patient has not requested the refill by the post-refill date, thereby indicating that the patient is more than X days late in requesting a refill of the prescription, the routine 400 initiates an intervention into the patient's medication therapy regimen as described further below. In another example, the routine 400 may determine compliance using the Medication Possession Ratio (MPR), where the MPR is a measure of adherence to a medication. The MPR may be determined from the number of pills on the shelf versus the days since the last prescription fill (last fill date plus days' supply) minus the first fill date. If the MPR falls below a threshold value, the routine 400 may initiate an intervention into the patient's medication therapy regimen.

If the patient has requested a refill of the prescription, as determined at block 410, the routine 400 determines whether or not the patient has actually refilled the prescription by the post-refill date. As is known, a patient may refill a prescription by picking up the prescription at a pharmaceutical store 22 or having the prescription delivered to the patient. When a refill has occurred, the refill and the date thereof may be noted in the analytics database 26. If the patient has refilled the prescription by the post-refill date, as determined at block 412, control may revert back to the medication therapy management routine 100. On the other hand, if the patient has not refilled the prescription by the refill date (i.e., the patient is more than X days late in refilling the prescription), the routine 400 initiates an intervention into the patient's medication therapy regimen.

In addition to determining whether a patient has requested a refill or refilled a prescription or whether a patient is late in requesting or refilling a prescription, the medication therapy regimen compliance routine 400 may also predict whether or not a patient may be non-compliant with a medication therapy regimen. Such predictions may be based on the patient's prescription history as provided with the medication data, including, but not limited to, the patient's previous compliance with other medications or medication therapy regimens, the patient's diligence in requesting refills and refilling previous or existing prescriptions and other trending data. Such prescription history data may be represented by previous refill dates, previous refill request dates, and previous dates of executing the refill, notes or codes indicating persistent non-compliance (e.g., consistently late in requesting or refilling a prescription) or indicating compliance (e.g., consistently on time, only a few instances of noncompliance, etc.). Further, the prescription history may also include prescription histories of similar patients (e.g., age, gender, family relationships) that have had similar medications or medical conditions (e.g., Alzheimer's).

Based on the prescription history data, the routine 400 predicts the patient's adherence to the medication therapy regimen at block 414, including, but not limited to whether or not the patient will be consistently late in requesting and refilling a prescription. The results of such a prediction may be provided to the analytics database 26 at block 416, and the routine 400 may determine whether an intervention is necessary at block 418. If not, control may revert back to the medication therapy management routine 100. Otherwise, if the routine 400 determines that an intervention is necessary based on the patient's predicted compliance with the medication therapy regimen, the routine 400 initiates an intervention.

At block 420, the medication therapy regimen compliance routine 400 creates a contact queue for all patients requiring intervention. The contact queue may be generated each day, and may also be generated for the pharmaceutical store 22 that administers the patient's prescription. The same or a different contact queue may be generated for the pharmaceutical care center 20. Generally, the contact queue is a list of patients to contact for intervention and may include the reasons for the intervention and an indication of whether the patient is new to a medication therapy regimen, predicted to be non-compliant, late in requesting a refill of the prescription or late in refilling the prescription. The patients in the contact queue may be grouped according to new-to-therapy, late refill requests, late refills and predicted noncompliance as a result of blocks, 404, 410, 412, 418, respectively. Accordingly, different groups may be created based on a degree of noncompliance, with the patients arranged in the contact queue based on their respective grouping.

Based on the contact queue, a user, such as a pharmacist and/or a pharmaceutical care center personnel, may be prompted to contact the patient or otherwise intervene in the patient's medication therapy regimen. The prompt may be provided in the form of a list generated in a print-out or generated on a computer display of all the calls or contacts the user is to make for a particular day for those patients that are late in requesting or re-ordering a refill of a prescription or that have requested a refill but are late in refilling the prescription. The print-out or display may include a code indicating the circumstances of the intervention (e.g., ">7DLRF"—greater than 7 days late, the medication(s) involved, reasons for adhering to the medication therapy regimen, etc). As such, the prompts may occur daily and result in the user intervening as provided by the intervention routine 800. The prompts may also occur on an event basis, such as when the patient picks up a prescription. For example, for patients new to a medication therapy regimen a receipt associated with the purchase of the medication may include an indication that the patient is new to the medication therapy regimen (e.g., "NTT™"—New to Therapy). Likewise, a patient predicted to be non-compliant with a medication therapy regimen may result in a corresponding indication on a purchase receipt when the patient picks up the prescription. The indications on the receipt may prompt the pharmacist to intervene as provided by the intervention routine 800.

Figure 6:
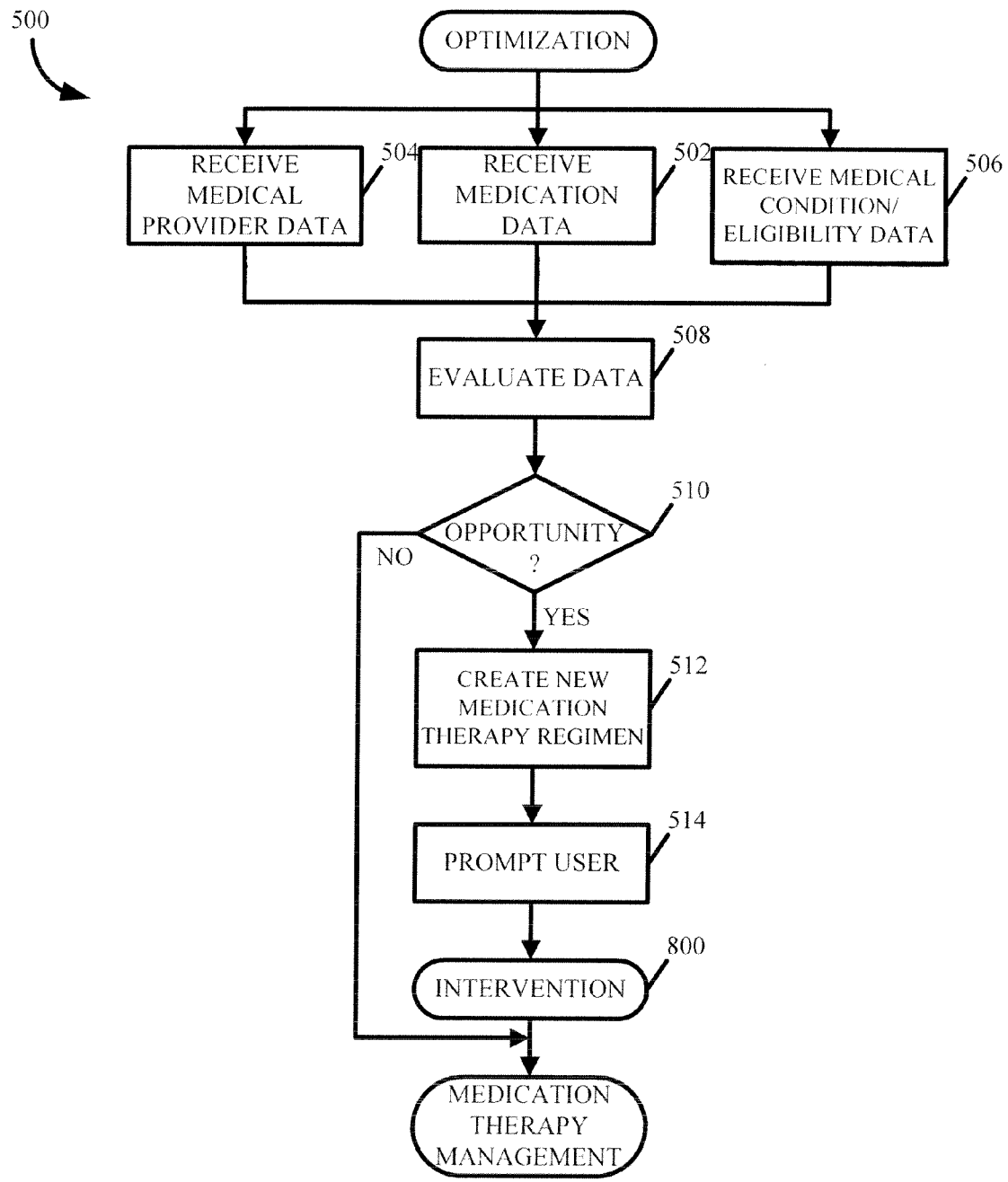
FIG. 6 is a flowchart of an embodiment of a medication therapy regimen optimization routine to determine opportunities to optimize the medication therapy regimen.

FIG. 6 illustrates an example of a medication therapy regimen optimization routine 500 shown schematically in FIG. 2. As previously indicated, the medication therapy regimen optimization routine 500 may be used to optimize a patient's medication therapy regimen by analyzing the medication therapy regimen, identifying opportunities for optimization and modifying the medication therapy regimen. The medication therapy regimen optimization routine 500 is particularly useful for those patients, such as elderly patients, having multiple medications, multiple medical conditions and/or multiple medical providers. The medication therapy regimen optimization routine 500 may be executed by a Retrospective Drug Use Review (RDUR) clinical Decision Support System (DSS), a pharmaceutical store 22 and/or a pharmaceutical care center 20 or clinic pharmacy.

Beginning at block 502, the medication therapy regimen optimization routine 500 receives medication data relating to one or more medications being used by the patient. Examples of the medication data that may be utilized by the medication therapy regimen optimization routine 500 include, but are not limited to, the name of the medication, medical effect, potential side effects, potential interactions with other medications, reasons for the medication such as medical conditions the medication is meant to address (e.g., a valid indication), the patient's duration of use and the patient's utilization of a medication such as a rate or amount of use, rate or amount of refills, medication dosage, cost, instructions for administering the medication, medication strength, etc.

Optionally, at block 504, the routine 500 may receive medical provider data relating to one or more medical providers associated with the patient, including doctors, hospitals, clinics and home care services which may provide the patient with medical examinations, medical treatment and/or prescribe medications, and at block 506, the routine 500 may receive medical condition data relating to one or more medical conditions such as drug inferred diseased states, medical claims data and/or medical history or diagnoses associated with the patient. In addition to receiving medical condition data at block 506, the routine 500 may receive eligibility data to verify or determine whether the patient is eligible for the service.

Generally, the data received at blocks 502, 504, 506 may be received by retrieving the patient file created at block 112 of the medication therapy management routine 100. Alternatively or in addition, some or all of the data received at blocks 502, 504, 506 may be received from an employer/healthcare insurer 24, medical provider and/or pharmaceutical store 22.

At block 508, the medication therapy regimen optimization routine 500 evaluates the medication data, and may further evaluate the medical provider data and/or the medical condition data, for potential opportunities for optimization. The evaluation at block 508 may initially include evaluating the patient's data for specific criteria to identify and stratify those patients having, but not limited to, multiple medical providers, multiple medications and/or multiple medical conditions. In one example, the routine 500 may only consider the medication therapy regimen to have an opportunity for intervention only if there are multiple providers, multiple medications, multiple medical conditions or combinations thereof. For instance, one criteria may include identifying only those patients having five or more unique medications within a 90-day period, patients having three or more medical providers that prescribe medications, and patients that have three or more medical conditions. Another criteria may include identifying only those patients having ten or more unique medications within a 90 day period. The inclusion of a specific time period may indicate the medical condition is chronic as opposed to a one-time occurrence. The criteria may further require that the patient have one or more specific medical conditions, including, but not limited to, asthma, psychological disorders, heart failure, diabetes, hypertension, cholesterol, pulmonary diseases, arthritis and ulcer disorders.

Further, the evaluation may include predictive modeling such as determining potential interactions between various medications being used by the patient, and interactions between a medication and a medical condition. The evaluation at block 508 may also identify instances of over-utilization or underutilization, identify medications which may no longer be required, are duplicative or otherwise redundant. Potentially adverse health outcomes may be identified, including side effects, hazardous interactions, For each identified, potentially adverse health outcome, the severity of the adverse health outcome may be determined. Based on the reasons for a medication, the evaluation may identify any medications that are without indication (i.e., no reason for the medical to have been prescribed), which may include, but are not limited to, inappropriate medications identified as described further below, Beers drugs (i.e., inappropriate drugs for elderly patients), drugs combinable into a single drug and three-times a day drugs.

Still further, the evaluation at block 508 may evaluate the cost associated with the patient's medication therapy regimen, including the cost of each medication individually and the total cost of the medication therapy regimen. For example, the evaluation may be used to identify only those patients having a total medication therapy regimen cost of over $4000 per year, or any other threshold amount. Although the evaluation may be conducted in all or in part by a software routine, in some instances the evaluation requires the expertise of a professional such as a pharmacist. As such, all or part of the evaluation may be conducted by a pharmacist, such as a pharmacist at the pharmaceutical store 22 or at the pharmaceutical care center 20. The result from the evaluation of the medication therapy regimen may include a Personal Medication Record, which includes a list of the medications included in the medication therapy regimen and an explanation of the effects and any potential areas where the regimen may be optimized or otherwise improved. Ultimately, the Personal Medication Record is preferably shared with the patient to further the patient's understanding of the medication therapy regimen, as described further below.

The evaluation at block 508 may also be based upon treatment guidelines, or other industry recognized standards, for one or more of the medical conditions identified from the medical condition data. In one example, the industry-recognized Medication Appropriateness Index may be used for evaluation. In a further example, the treatment guidelines are established by quality watch group such as a professional organization of pharmacists, medical providers and/or healthcare insurers 24. Alternatively or in conjunction, the treatment guidelines may be established based on an established medical board, and/or among the participants of the medication therapy regimen management service, examples of which were provided above. Examples of national treatment guidelines for treating particular medical conditions include:

The Seventh Report of the Joint National Committee on Prevention, Detection, Evaluation, and Treatment of High Blood Pressure: The JNC 7 Report. JAMA. 2003; 289 (19): 2560-71.

The third report of the National Cholesterol Education Program (NCEP) Expert Panel on Detection, Evaluation, and Treatment of High Blood Cholesterol in Adults (Adult Treatment Panel III) Executive Summary. National Cholesterol Education Program. National Heart, Lung, and Blood Institute. National Institutes of Health. NIH Publication No. 01-3670. May 2001.

National Heart, Lung, Blood Institute. National Asthma Education and Prevention Expert Panel Report 2. Guidelines for the Diagnosis and Management of Asthma. Update on Selected Topics 2002. NIH Publication No. 02-5074. June 2003.

ACC/AHA Guidelines for the Evaluation and Management of Chronic Heart Failure in the Adult, J Am Coll Cardiol 2001; 38: 2101-13.

Global Strategy for the Diagnosis, Management, and Prevention of Chronic Obstructive Pulmonary Disease. GOLD Expert Panel: The Global Initiative for Chronic Obstructive Lung Disease (GOLD) Workshop Report. Updated 2005 (Based on an April 1998 NHLBI/WHO Workshop).

Beta-Blocker Heart Attack Trial Research Group. JAMA. 1982; 247:1707-1714, AND Norwegian Mulitcentre Study Group. N Engl J Med. 1981:304:801-807

U.S. Department of Health and Human Services. Bone Health and Osteoporosis: A Report of the Surgeon General. Rockville, Md.: U.S. Department of Health and Human Services, Office of the Surgeon General, 2004.

Gudbjornsson B, Juliusson U I, Gudjonsson F V. Prevalence of long-term steroid treatment and the frequency of decision making to prevent steroid-induced osteoporosis in daily clinical practice. Ann Rheum Dis 2002; 61(1): 32-36.

Although the examples of the national treatment guidelines provided above include examples of various medical conditions and various sources of treatment guidelines, the medical conditions are not limited thereto. Further, the sources of the national treatment guidelines are not limited to the examples above, and different sources of treatment guidelines may be provided for any of the medical conditions mentioned above or in addition to those medical conditions mentioned above.

The treatment guidelines data may include, but is not limited to, medications for particular medical conditions, medication strengths, instructions for administering the medications, medical treatment for particular medical conditions, and tests or examinations generally administered for the medical condition. The treatment guidelines are provided as inputs to the routine 500 and are the basis for any recommended changes resulting from the routine 500. The treatment guidelines may be updated on a periodic basis to maintain adherence to the most up-to-date standards of health care.

Based on the evaluation at block 508, the medication therapy regimen optimization routine 500 determines whether or not opportunities exist to optimize or otherwise improve the patient's medication therapy regimen at block 510. If not, control may revert back to the medication therapy management routine 100. However, if one or more opportunities exist to optimize the medication therapy regimen, the routine 500 may determine a new medication therapy regimen at block 512. In some instance, creation of a new medication therapy regimen may include modifying the patient's existing medication therapy regimen.

The creation of a new medication regimen at block 512 may include removing and/or replacing one or more medications with a new medication. For example, a medication may be removed if it is duplicative of another medication, if the medication is no longer required (e.g., the associated medical condition no longer exists), if the removal of the medication will improve the medical effect of the other medications without adversely affecting the patient, if the removal will reduce or eliminate an undesired side effect or if the medication was without indication. A medication may be replaced with another medication, including replacing a brand name medication with a lower cost, equivalent generic medication, if available.

In addition to creating a new medication therapy regimen for the patient, the routine 500 may further evaluate the new medication therapy regimen to identify any potentially adverse health outcomes, the risk associated with the identified, potentially adverse health outcome, the likelihood of such outcomes, or otherwise evaluate the new medication therapy regimen in a manner similar to the evaluation of the existing medication therapy regimen as was performed at block 508. Accordingly, the creation of a new medication therapy regimen at block 512 includes an optimization check for any further opportunities for optimization. The result from the creation of a new medication therapy regimen may include a new Personal Medication Record, which may include, but is not limited to, a list of the medications included in the medication therapy regimen, medication name, medication strength, what the medication is used for, instructions for administering the medications and an explanation of the benefits as compared to the previous medication therapy regimen.

At block 514, the routine 500 prompts a user, such as the patient's pharmacist or a pharmacist at a pharmaceutical care center 20, to intervene in the patient's medication therapy regimen to execute the new medication therapy regimen. As above, the user may be prompted by a daily print-out of interventions to be conducted for that day, a prompt on a computer display, a prompt when the patient refills a prescription, etc. The intervention may be conducted in accordance with the intervention routine 800.

Figure 7:
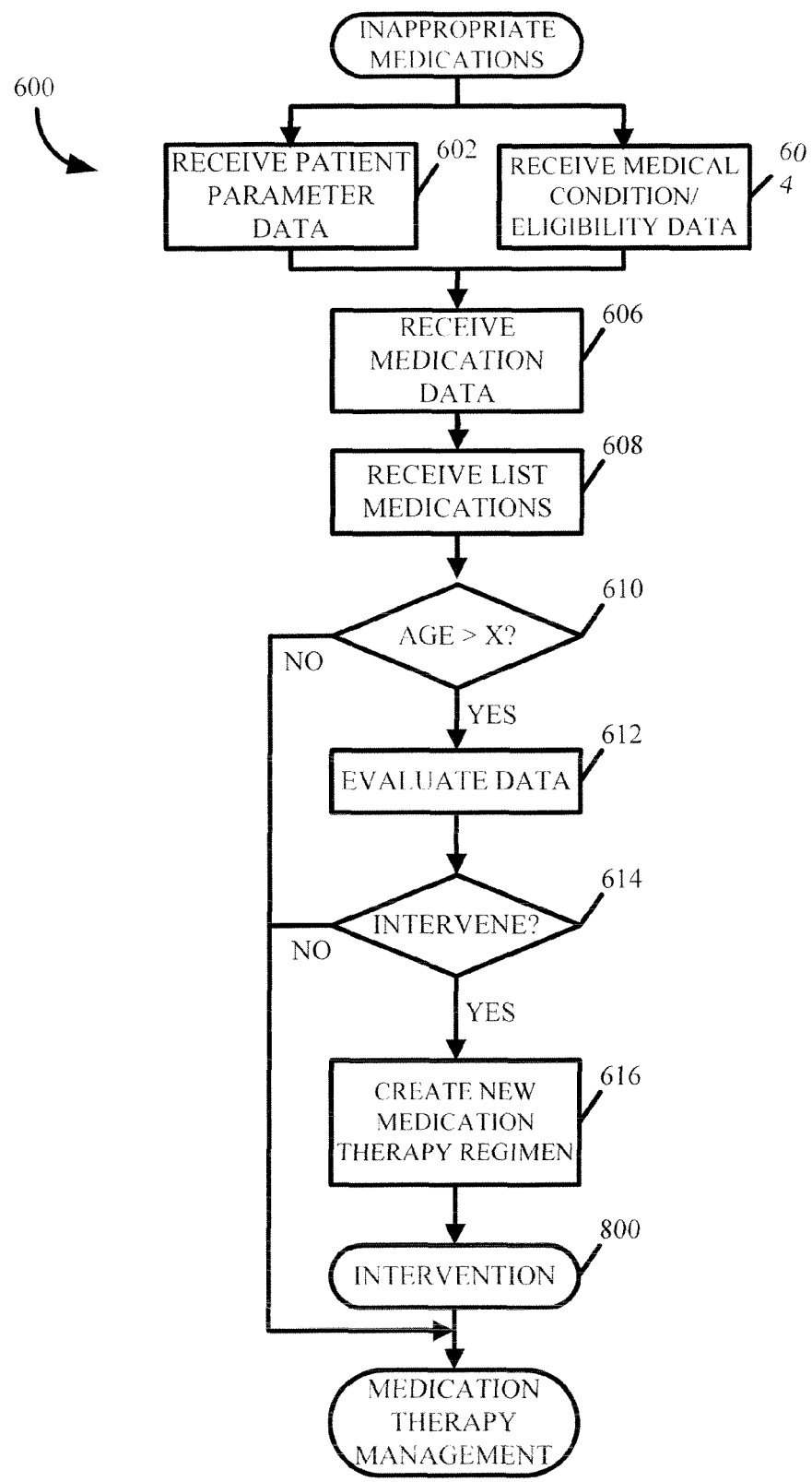
FIG. 7 is a flowchart of an embodiment of an inappropriate medications routine to identify inappropriate medications within the medication therapy regimen.

FIG. 7 illustrates an example of an inappropriate medications routine 600 shown schematically in FIG. 2. As previously indicated, the inappropriate medications routine 600 may be used to identify inappropriate medications in a patient's medication therapy regimen, and, in particular, identify inappropriate medications in an elderly patient's medication regimen given medical conditions associated with the elderly patient. For example, particular medications, sometimes referred to as Beers drugs, are known to have high risk adverse effects in elderly patients. Other medications are also known to have adverse effects in elderly patients, but are lower risk. Accordingly the inappropriate medications routine 600 identifies such inappropriate medications to prevent potentially adverse health effects or unintended consequences in the patient. Modifications to the medication therapy regimen may be conducted, similar to the medication therapy regimen optimization routine to remove and/or replace an inappropriate medications.

Beginning at block 602, the inappropriate medications routine 600 receives patient parameter data, including, but not limited to, the patient's name, contact information (e.g., address, electronic address, telephone number, etc.), medical provider(s), etc. The patient parameter data may further include patient risk factor data which may be used to assess a health risk of the patient. The patient risk factor data may include, but is not limited to, age, ethnicity, gender, genetic predisposition and weight. Optionally, at block 604, the routine 600 may receive medical condition data relating to one or more medical conditions associated with the patient. At block 606, the routine 600 receives medication data relating to one or more medications being used by the patient. Examples of the medication data that may be utilized by the medication therapy regimen optimization routine 600 include, but are not limited to, the name of the medication, medical effect, potential side effects, potential interactions with other medications, reasons for the medication such as medical conditions the medication is meant to address (e.g., a valid indication), the patient's duration of use and the patient's utilization of a medication such as a rate or amount of use, rate or amount of refills, medication dosage, cost, instructions for administering the medication, medication strength, etc. Generally, the data received at blocks 602, 604, 606 may be received by retrieving the patient file created at block 112 of the medication therapy management routine 100. Alternatively or in addition, some or all of the data received at blocks 602, 604, 606 may be received from an employer/healthcare insurer 24, medical provider 12, 14, 16, 18 and/or pharmaceutical store 22.

At block 608, the routine 600 receives data relating to a list of medications that are inappropriate for elderly patients. As an example, the inappropriate medications data may include a list of Beer drugs, which include, but are not limited to, chlordiazepoxide, chlorazepate, diazepam, quazepam, halesepam, meprobamate, flurazepam, chlorpropamide, meperdine, propoxyphene, amitryptiline, doxepin, trimpramine and imipramine. Such a list may be maintained by the medication therapy management routine 100 in the analytics database 26, and updated as new medications are added or removed. Additional medications may also be received at block 608, even those they may be of reduced risk of adverse health outcomes as compared to Beers drugs, but which nonetheless may have a risk of significant undesired effects on the patient.

As previously indicated, the routine 600 is particularly useful with elderly patients, and even more particularly with elderly patients having reduced liver or kidney functions. Accordingly, at block 610, the inappropriate medications routine 600 may determine whether the patient's age exceeds a predetermined threshold in order to be considered an elderly patient. The determination at block 610 may be based on the patient's age and/or date of birth as provided with the age data If the patient's age does not exceed a predetermined threshold, control may revert back to the medication therapy management routine 100. Otherwise, the patient's medication data may be evaluated at block 612, along with the patient's medical condition data, if provided.

The evaluation at block 612 may identify those patients having reduced liver or kidney functions, or other particular medical conditions based on the medical condition data. For such patients, the evaluation may further include evaluating the medication data to determine if there is a risk of an adverse health outcome, and to determine the severity of that risk. In particular, the evaluation at block 612 may compare the medications from the medication data with the list of medications received at block 608. If the patient's medication match one or more of the medications from the list of medications, the evaluation may determine the level of risk associated with the matching medications.

Accordingly, at block 614, the inappropriate medications routine 600 determines whether an intervention is necessary based on the evaluation at block 612. For example, if the patient does not have a reduced liver or kidney function, or if the patient's medications did not include a medication from the list of inappropriate medications, an intervention may not be required, and control may revert back to the medication therapy management routine 100. However, if an intervention is required, the inappropriate medications routine 600 may proceed to establish a new medication therapy regimen for the patient at block 616.

The new medication therapy regimen created at block 616 may involve removing the inappropriate medication, and/or replacing the inappropriate medication with a new medication having a comparable medical effect without the attendant adverse health outcome. The new medication may also be compared to the list of inappropriate medications to determine if the new medication will cause a different adverse health outcome. Once the new medication therapy regimen has been established, the intervention may be conducted in accordance with the intervention routine 800.

Figure 8:
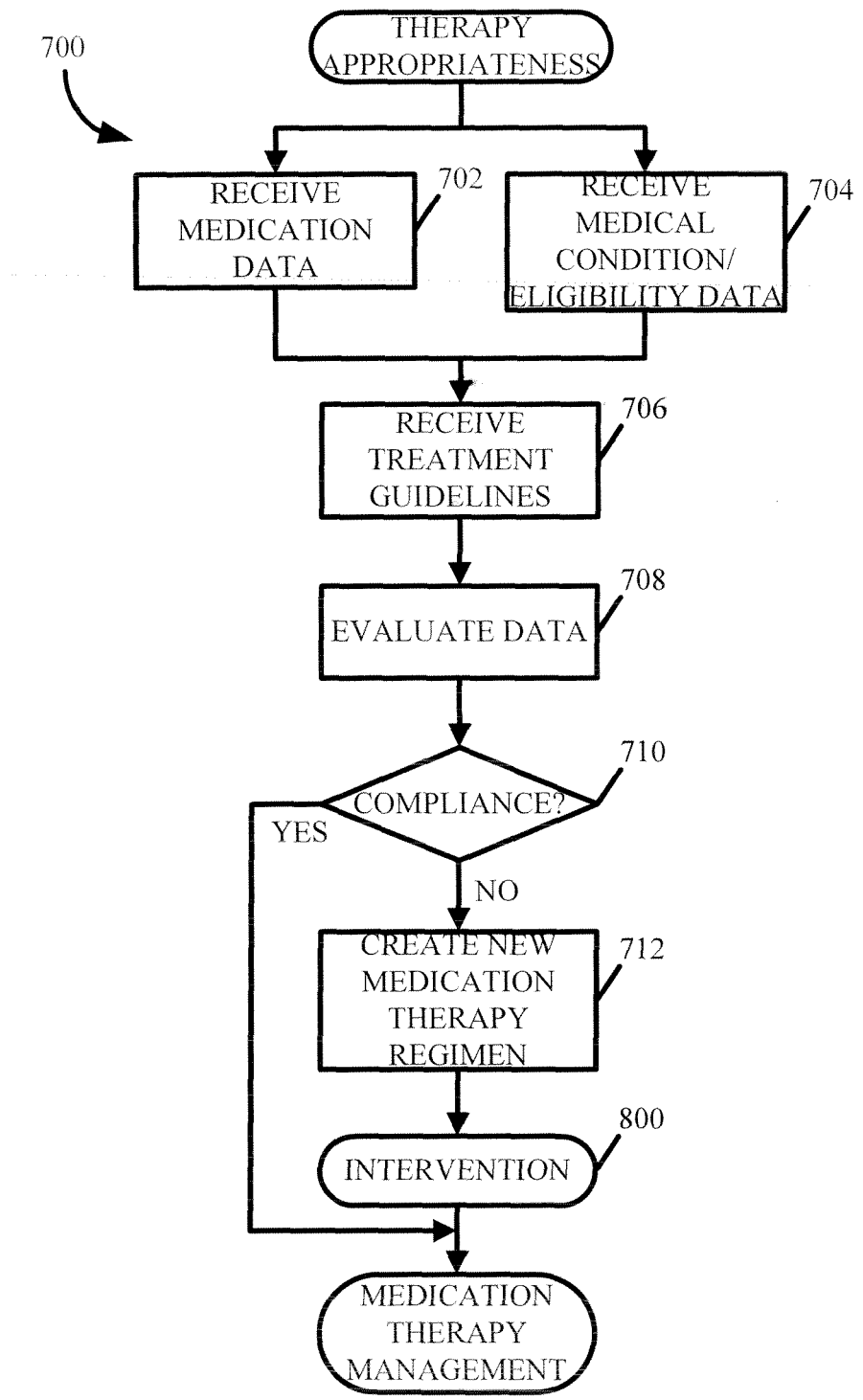
FIG. 8 is a flowchart of an embodiment of a medication therapy regimen appropriateness routine to determine compliance with treatment guidelines.

FIG. 8 illustrates an example of a medication therapy regimen appropriateness routine 700 shown schematically in FIG. 2. As previously indicated, the medication therapy regimen appropriateness routine 700 may be used to identify patients that may be receiving sub-optimal care based on established standards of care, such as nationally established guidelines for treating particular chronic illnesses. Although the medication therapy regimen appropriateness routine 700 may be executed across the data network 10, in one example, the medication therapy regimen compliance routine 400 is executed by the Retrospective Drug Use Review (RDUR) clinical Decision Support System (DSS).

Beginning at block 702, the medication therapy regimen appropriateness routine 700 receives medication data relating to one or more medications being used by the patient. Optionally, at block 704, the routine 700 may receive medical condition data relating to one or more medical conditions associated with the patient. Examples of the medication data that may be utilized by the medication therapy regimen appropriateness routine 700 include, but are not limited to, the name of the medication, medical effect, potential side effects, potential interactions with other medications, reasons for the medication such as medical conditions the medication is meant to address (e.g., a valid indication), the patient's duration of use and the patient's utilization of a medication such as a rate or amount of use, rate or amount of refills, medication dosage, cost, instructions for administering the medication, medication strength, etc. Examples of the medical condition data may include, but are not limited to, specific medication conditions or ailments of the patient, patient medical examinations and the results thereof, medical treatment, blood tests, genetic tests, or other medical analyses. Generally, the data received at blocks 702, 704 may be received by retrieving the patient file created at block 112 of the medication therapy management routine 100, or may be received directly from an employer/healthcare insurer 24, medical provider 12, 14, 16, 18 and/or pharmaceutical store 22.

At block 706, the routine 700 receives data relating to treatment guidelines for one or more of the medical conditions identified from the medical condition data. In one example, the treatment guidelines are established by quality watch group such as a professional organization of pharmacists, medical providers and/or healthcare insurers 24. Alternatively or in conjunction, the treatment guidelines may be established based on an established medical board, and/or among the participants of the medication therapy regimen management service, examples of which were provided above.

The treatment guidelines data may include, but is not limited to, medications for particular medical conditions, medication strengths, instructions for administering the medications, medical treatment for particular medical conditions, and tests or examinations generally administered for the medical condition. The treatment guidelines are provided as inputs to the routine 700 and are the basis for any recommended changes resulting from the routine 700. The treatment guidelines may be updated on a periodic basis to maintain adherence to the most up-to-date standards of health care.

At block 708, the routine 700 evaluates the medication data and the treatment guidelines data, and may further evaluate the medical condition data, to determine a level of compliance between the medical treatment being received by the patient and the treatment guidelines. The level of compliance is representative of the appropriateness of the treatment being received by the patient for the medical condition, and particularly for chronic medical conditions. For example, the treatment guidelines may require that the patient receive particular medication treatment for a condition, including particular medications. Examples of chronic medical conditions which may be evaluated include diabetes, heart failure, asthma and oral steroid use. Examples of appropriate medications for the treatment of such chronic medical conditions include statins, beta blockers, Ace-I inhibitors, Angiotensin II receptor blockers, long-term asthma controllers and bisphosphonates. For instance, if the patient medical condition data indicates the patient has, for example diabetes but does not include a statin, an Ace-I inhibitor or an Angiotensin II receptor blocker, the evaluation at block 708 may determine that the patient's medical treatment does not comply with the treatment guidelines. If there exists noncompliance between the patient's actual medical treatment and the treatment guidelines, the evaluation may further include determining a level of risk associated with continuing the patient's existing medication therapy regimen, such as the risk of an adverse health outcome.

At block 710, the routine 700 determines if there was full compliance with the treatment guidelines as evaluated at block 708. If so, control may revert back to the medication therapy management routine 100. Otherwise, the routine 700 may create a new medication therapy regimen at block 712. The new medication therapy regimen created at block 712 may involve prescribing or otherwise including an appropriate medication to treat the medical condition in compliance with the treatment guidelines. In addition, the creation of a new medication therapy regimen may include removing or replacing an existing medication being used to treat the medical condition, but which does not comply with the treatment guidelines. Once the new medication therapy regimen has been established, the intervention may be conducted in accordance with the intervention routine 800.

Figure 9:
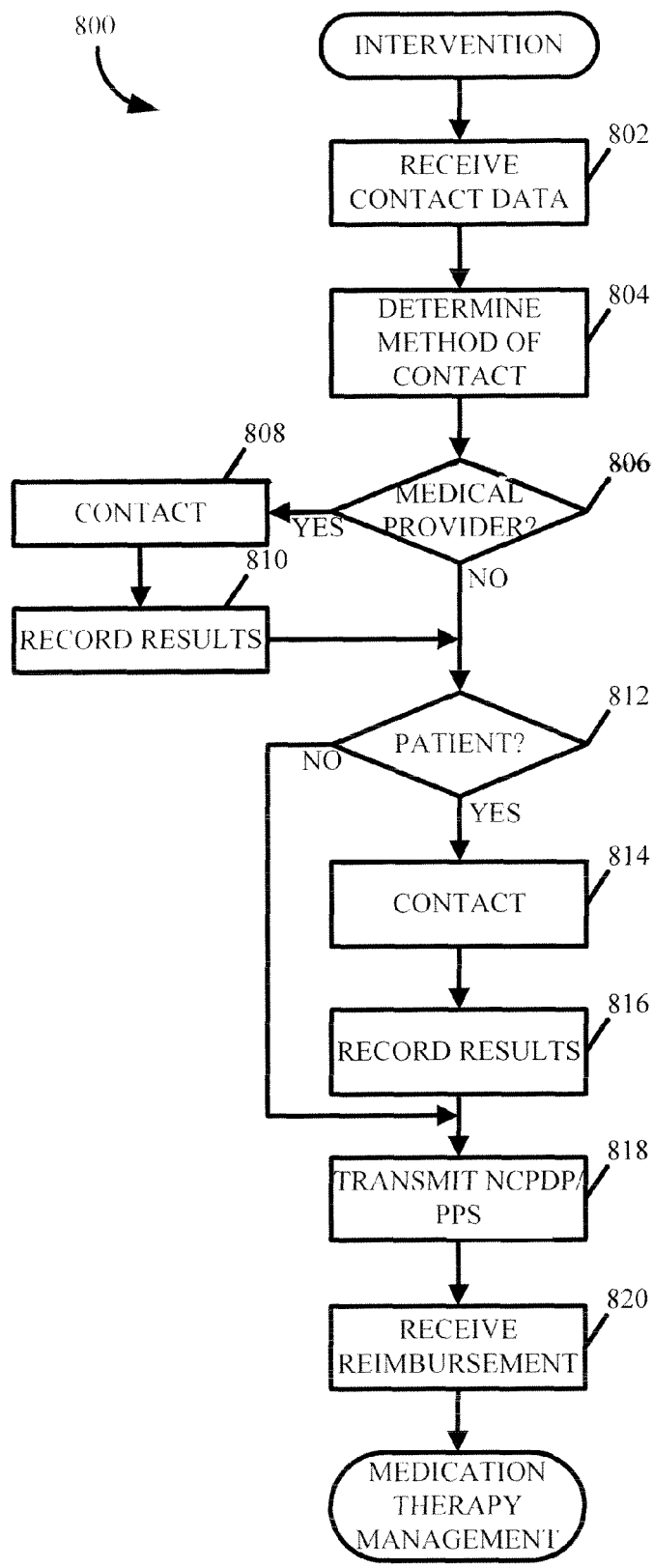
FIG. 9 is a flowchart of an intervention routine to intervene in the mediation therapy regimen.

FIG. 9 illustrates an example of an intervention routine 800 shown schematically in FIGS. 3-8. The intervention routine 800 may be used whenever one of the routines 200, 300, 400, 500, 600, 700, determines that an intervention into a patient medication therapy regimen is necessary. As will be described further below, the form of intervention (e.g., point-of-sale, face-to-face, telephone, facsimile, electronic mail, etc.) may depend on the urgency of the intervention and/or the type of intervention. Further, while the intervention may primarily occur with the patient, the intervention may also occur with respect to third parties, such as the patient's medical provider. In some cases, contacting the patient's medical provider may occur first in order to consult the medical provider and proceed based on the medical provider's advice and recommendations. In addition to intervening in the patient medication therapy regimen, the intervention routine 800 may also be provided to reimburse a user for services provided in relation to the intervention. All or part of the intervention routine 800 may be performed by the patient contact management 32 in conjunction with one or more of the pharmaceutical store 22 and the pharmaceutical care center 20. As such, when an intervention is identified from the routines 200, 300, 400, 500, 600, 700, each of the pharmaceutical stores 22 and pharmaceutical care centers 20 within the data network 10 may be apprised of the intervention requirement by the patient contact management 32. In the event a particular pharmaceutical store 22 utilized by the patient is not within the data network 10, the patient contact management 32 may attempt to match the data network 10 with a network, such as a prescription network, associated with the nonparticipating pharmaceutical store 22.

As explained above, intervention in a patient's medication therapy regimen may occur under a variety of circumstances, including identification of potentially adverse health outcome(s), noncompliance, predicted noncompliance, new to therapy, modifications to an existing medication therapy regimen, etc. Specifically, a pharmacist at pharmaceutical store 22 and/or a pharmaceutical care center 20 may contact the patient, the patient's medical provider (e.g., a medical provider prescribing the medication), or both in an effort to inform the patient of recommended changes to the medication therapy regimen, consultations on the importance of adhering to the medication therapy regimen, prevention of an identified, potentially adverse health outcome, educate the patient regarding an existing or new medication therapy regimen, etc. Such communication between the pharmacist and the medical provider and/or patient may take place via telephone, mail, electronic mail, facsimile, etc., or any combination thereof. Further, a system, such as the patient contact management 32, may automatically generate such communications.

Such an intervention may take place initially, e.g., when subscribers subscribe to the service and the relevant medical condition and medication data becomes available. Thereafter, this service can be provided at random or at calculated intervals. Alternatively, the service can be provided each time a patient has a prescription filled at the pharmaceutical store 22. In one example, a patient may have a communication device which may be operatively coupled to the data network 10 (e.g., via a website), thereby enabling a patient to order or submit prescriptions with a pharmaceutical website. Access to the retail pharmacy web site may be made available via the Internet, where a patient may enter a unique customer ID or other personal information to access the patient file. This allows the patient to submit or order prescriptions from the pharmaceutical store 22 without having to physically visit the store. In addition, this allows the patient to update his/her pharmacist with regard to additional, previously undisclosed medical condition data or medication data. Alternatively, the patient may be given a mail-in account update form so that the patient may complete the mail-in form and send it to the pharmaceutical store 22 or pharmaceutical care center 20 to perform an update of his/her file. Upon receipt by the pharmaceutical store 22 or pharmaceutical care center 20 of the patient's prescription or other information, the new medication data, medical condition data or other information may be entered into the patient's file, and the medication therapy management routine 100 may conduct medication therapy management services in light of the additional information may be performed.

Referring to FIG. 9 and beginning at block 802, the intervention routine 800 receives contact data relating to one or more people to contact for the intervention. The contact data may be retrieved from the patient's profile, from data provided by the medical provider and/or from data provided from the employer/healthcare insurer 24. The contact may include, but is not limited to, the name of the contact (e.g., patient, medical provider), available methods of contact (e.g., scheduled appointment, face-to-face, telephone, facsimile, electronic mail, etc.). The contact data may also specify who will initiate the intervention and contact the patient. While interventions may be performed by a pharmacist at a pharmaceutical store 22, by a pharmacist or associate at a pharmaceutical care center 20, by a medical provider associated with the patient or any combination thereof, the pharmaceutical care center 20 may further function as a back-up for any interventions that were identified but not otherwise conducted.

At block 804, the intervention routine 800 determines the particular method of contact, which may be based on the particular type of intervention involved or reasons for the intervention. For example, interventions resulting from the health risk assessment routine 200 may depend on the severity of risk involved with an identified, potentially adverse health outcome and the likelihood of the adverse health outcome occurring. A highly severe identified, potentially adverse health outcome (e.g., disablement or death) with even a low or moderate likelihood of occurring (e.g., %10) may result in having both the pharmaceutical store 22 and the pharmaceutical care center 20 contact both the medical provider and the patient by as many means as possible. By contrast, an identified, potentially adverse health outcome having a low severity of risk (e.g., minor discomfort) with a moderate to high likelihood of occurring (e.g., 50%) may result in a pharmacist at the pharmaceutical store 22 consulting the patient the next time the patient picks up a prescription, or the pharmaceutical care center 20 contacting the patient by telephone.

Interventions resulting from the modeling and risk stratification routine 300 may be dependent on the level of intervention determined during the routine 300, in addition to the severity of risk involved with an identified, potentially adverse health outcome and the likelihood of the adverse health outcome occurring. For example, a high level of interaction may including having both the pharmaceutical store 22 and the pharmaceutical care center 20 contact both the medical provider and the patient may as many means as possible. On the other hand, a low level of interaction may result in a pharmacist at the pharmaceutical store 22 consulting the patient the next time the patient picks up a prescription, or the pharmaceutical care center 20 contacting the patient by telephone.

Interventions resulting from the medication therapy regimen compliance routine 400 may be dependent on the compliance issue involved. For example, a patient new to a medication therapy regimen may receive an intervention via a pharmacist at a pharmaceutical store 22, which may be face-to-face when the patient fulfills an associated prescription or by telephone. In another example, if the medication therapy regimen compliance routine 400 predicts that a patient will be noncompliant, the intervention routine 800 may determine that the pharmaceutical care center 20 should contact the patient. Patients that have requested a refill of a prescription but are late in actually refilling the prescription may receive an intervention via a pharmacist at a pharmaceutical store 22 (e.g., a point-of-sale intervention) either when the patient finally fulfills the prescription or by telephone. On the other hand, patients that are late in refilling the prescription in addition to being late in requesting a refill of the prescription may be contacted by both the pharmaceutical store 22 and the pharmaceutical care center 20. As previously indicated, a daily contact queue may be generated for the pharmaceutical store 22s 22 and the pharmaceutical care centers 20 which may indicate the order in which to contact patients, the method of intervention, the particular type of intervention, the reasons for the intervention or any combination thereof.

Interventions resulting from the medication therapy regimen optimization routine 500 may necessarily involve contacting and collaborating with the patient's medical provider before contacting the patient, if the routine 500 has created a new medication therapy regimen for the patient. Further, an intervention resulting from the medication therapy regimen optimization routine 500 may be dependent on the severity of risk associated with any potential adverse health outcome. For example, a high risk identified, potentially adverse health outcome may result in a both the pharmaceutical store 22 and the pharmaceutical care center 20 contacting the medical provider and the patient. On the other hand, a modification to the medication therapy regimen that replaces a brand name medication with a lower cost generic medication may result in the pharmaceutical store 22 and/or pharmaceutical care center 20 contacting the patient to schedule an appointment between a pharmacist and the patient. In one example, the pharmaceutical care center 20 may establish a list of such patients to contact, and a pharmacy technician or other personnel within a pharmaceutical store 22 may contact the patient to set up an appointment, during which a pharmacist (e.g., a regional pharmacists specifically trained in medication therapy management) performs a face-to-face intervention with the patient.

Interventions resulting from the inappropriate medications routine 600 may generally require immediate intervention because of the potentially high risk associated with particular medications. Accordingly, the method of contact determined at block 804 may include immediately contacting the patient and/or the patient's medical provider by a variety of methods, including telephone, electronic mail, etc. Further, the intervention may include denying the patient a refill on a prescription associated with the inappropriate medication when the patient attempts to refill the prescription (e.g., point-of-sale). Low risk inappropriate medications may result in a letter being sent to the patient and/or medical provider.

Interventions resulting from the medication therapy regimen appropriateness routine 700 may be dependent on the degree of compliance with treatment guidelines and the risk of the identified, potentially adverse health outcomes. For example, a high degree of compliance with the treatment guidelines having a high risk identified, potentially adverse health outcome may result in telephoning the medical provider and the patient. A moderate degree of compliance having a low risk of the identified, potentially adverse health outcomes may result in a letter or facsimile to the medical provider and a point-of-sale intervention with the patient.

Upon determining the method of contact based on the contact data and the results of the routines 200, 300, 400, 500, 600, 700, the intervention routine 800 determines whether the contact method involves contacting a medical provider, such as primary physician for the patient or a medical provider that prescribed a particular medication at block 806. If a medical provider is to be contacted, the routine 800 involves contacting the medical provider by the indicated method (e.g., telephone, facsimile, electronic mail, etc.). The contact with the medical provider may depend on the particular reasons for the intervention. For example, if a new medication therapy regimen has been developed thereby resulting in a new medication, and additional medication or removal of a medication as compared to the previous medication therapy regimen, the contact with the medical provider may include consulting the medical provider and soliciting recommendations, changes, approval, etc. regarding the new medication therapy regimen. In some cases, a medical provider may approve of the changes to the medication therapy regimen, object to the changes or have additional recommendations, including additional or alternative medications. In one example, the medical provider may be informed that a medical therapy management service was performed, such as an optimization of the patient's medication therapy regimen, in which case the medical provider may be provided with a list of the patient's medications, strengths, prescribed dosage and days supply, along with any additional over-the-counter medications and herbal supplements.

At block 810, the results of the contact with the medical provider are recorded with the analytics database 26, Retrospective Drug Use Review (RDUR) clinical Decision Support System (DSS) or other database. The results may include the date, time and method of contact, the name of the medical provider and patient, and the reasons for contacting the medical provider. Further the results may include any approval, disapproval, recommendations or changes made by the medical provider regarding the patient's medication therapy regimen. Still further, if the medical provider approves of changes to a medication therapy management or changes the medication therapy regimen, the results may include medication prescription relating to such changes. For example, a pharmaceutical store or pharmaceutical care center employee or pharmacist may update the patient's file by entering a minimal amount of information, such as, for example, the patient's name or unique customer ID and the contact results may be stored with or otherwise associated with the patient's file. In a case where the medical provider does not approve a change to the medication therapy regimen, but rather maintains the existing mediation therapy regimen, the results may include a notation or code to conduct another intervention at a particular date (e.g., one year later) or when the patient's medical provider changes.

Following block 810, or if a medical provider was not contacted as determined from block 806, the intervention routine 800 determines whether to contact the patient at block 812 in accordance with the contact methods determined at block 804 and/or in accordance with the medical provider's instructions from block 808. In some cases, only the medical provider may require contacting to satisfy the intervention in which case the patient does not require contacting. However, if the patient is to be contacted, as determined at block 812, the intervention routine 800 involves contacting the patient by the indicated method (e.g., telephone, facsimile, electronic mail, etc.). The contact with the patient may depend on the particular reasons for the intervention. For example, if a new medication therapy regimen has been developed, either from one of the routines 200, 300, 400, 500, 600, 700, or from previous contact with a medical provider at block 808, thereby resulting in a new medication, an additional medication or removal of a medication as compared to the previous medication therapy regimen, the contact with the patient may include providing the patient with a Personal Medication Record.

In one example, if the patient enrolls in the medication therapy management services as described above with reference to FIG. 2, the patient may receive a follow-up communication, such as a letter, enclosing and explaining the Personal Medication Record and a Medication Action Plan, both tailored to the patient. The Personal Medication Record may include a version for the patient and for the patient's pharmacist. The patient version of the Personal Medication Record may be provided as a dosage calendar. In particular, the patient version of the Personal Medication Record may provide a list of current medications prescribed by the patient's medical provider(s), and for each medication the Personal Medication Record may provide details about the medication, such as the medication name, strength, and description, such as the general shape and color of the medication, a tablet ID stamped onto the medication and/or a picture of the medication. In addition, the patient version of the Personal Medication Record may provide information on the medical condition (e.g., indication) the medication is being used to treat, along with instructions for administering the medication to achieve the optimal therapeutic result. For example, the instructions may include the time(s)/day(s) to administer the medication along with the corresponding dosage, along with any special instructions. Any medications that have been discontinued by the medical provider(s) as a result of the medical provider reviewing the patient medication profile may be listed as such in the Personal Medication Record. The patient version of the Personal Medication Record may distinguish between prescription medications, over-the-counter medications and herbal supplements that are part of the patient medication therapy regimen and list each according along with a list of the patient's allergies.

If one or more of the medication therapy management services have been performed for the patient resulting in a new medication therapy regimen, the patient version of the Personal Medication Record may further include information about the new medication therapy regimen, including, but not limited to, the names of the new medications, strengths, description of medication appearance, instructions for administering the medications, explanation of each medication's purpose or use, any side effects, reasons for the change, a comparison with the previous mediation therapy regimen including attendant benefits (e.g., reduced risks, reduced side effects, lower cost, etc.). The communication may further include executing the new medication therapy regimen, such as dispensing the associated prescriptions to the patient. Other patient contact may include consultation, such as explaining the importance of adhering to a medication therapy regimen, issues requiring consultation with a medical provider, an explanation of opportunities to change the medication therapy regimen such as optimization opportunities, etc.

The pharmacist version of the Personal Medication Record provides a list of changes to the patient's medication therapy which may require action by the pharmacist. In particular, the pharmacist version of the Personal Medication Record may include the medications (e.g., name, dosage, days supply) reviewed by the medication therapy management services, the recommended action for each of the medications (e.g., change dosage, provider alternative medication, discontinue, new therapy) along with changes to the medication therapy recommended by the medical provider (e.g., medication, effective date, dosage, days supply, contact information). The recommended changes may be provided as a result of contacting the medical provider above.

The Medication Action Plan provides a provides a summary of the medication profile review that was performed by the medication therapy management services, a list of pharmacist recommendations to enhance the patient's medication therapy regimen, and a list of the patient's prescription medications, emergency contacts, and any over-the-counter medications, herbal supplements and known allergies, which may be provided as an easy-to-carry card. The Medication Action Plan may further include a summary of the pharmacist's review of the patient's medication therapy regimen which lists the items that the participating pharmacist used to review the patient medication profile and the results of each review. In particular, the summary may include a listing those medications for which opportunities were identified to improve the patient's medication therapy regimen.

Referring back to FIG. 8, at block 816, the results of the contact with the patient are recorded with the analytics database 26, Retrospective Drug Use Review (RDUR) clinical Decision Support System (DSS) or other database. The results may include the date, time and method of contact, the name of the patient, and the reasons for contacting the patient. Further the results may include any approval, disapproval, recommendations or changes made by the patient regarding the medication therapy regimen, expressions of compliance or noncompliance, concerns, etc.

For each intervention performed, the pharmaceutical store 22, pharmaceutical care center 20, or pharmacist in particular, may receive payment or reimbursement for conducting the intervention. The amount of payment or reimbursement may be dependent on the type of intervention, reason for intervention, time involved in conducting the intervention, skill involved in the intervention or any combination thereof. For example, interventions resulting from the different routines 200, 300, 400, 500, 600, 700 may result in different payments or reimbursement. Accordingly, following an intervention with the patient and/or medical provider, the intervention routine 800 causes a reimbursement code to be submitted to the analytics database 26, and which may, in particular, be submitted to the invoice/billing service 36. The reimbursement code may be a code developed under the National Council for Prescription Drug Programs Professional Pharmacy Services (NCPDP/PPS code). Different reimbursement codes may be used for different reimbursement amount, as mentioned above. The analytics database 26, and/or invoice/billing service 36 receives the reimbursement code at block 820, and subsequently processes the payment to the pharmacists, pharmaceutical store 22 or pharmaceutical care center 20.

In addition to contacting the medical provider and/or the patient, the patient's pharmacist(s) may be kept apprised of the patient's medication therapy regimen and changes thereto. For example, when a patient enrolls in the medication therapy management services, the pharmacist may be provided with a Patient Consultation Package, which includes instructions, a service bill and consultation checklist, the pharmacist version of the Personal Medication Record, the patient version of the Personal Medication Record, the Medication Action Plan and a pharmacist satisfaction survey. The package may be provided to the pharmacist prior to one or more of the medication therapy management services. For example, prior to the medication therapy regimen optimization routine 500 the pharmacist may be instructed to review the documents provided in the package, schedule a consultation appointment with the patient to review the package with the patient and to request the patient to bring all prescription medications, over-the-counter medications and herbal supplements to the consultation. The pharmacist may be instructed to complete the service bill during the consultation and provided to the medication therapy management services provider in order to receive payment, as indicated at blocks 818 and 820 of FIG. 9. The pharmacist may be instructed to use the consultation checklist to ensure that the consultation is performed accurately and to ensure the proper materials are returned to the medication therapy management services provider for processing.

The pharmacist version of the Personal Medication Record may include medication therapy recommendations and/or changes to the patient's medication therapy regimen, as mentioned above. The pharmacist may be instructed to use this version of the Personal Medication Record during the consultation to present an overview of the recommended changes to the patient's medication therapy regimen and questions designed to capture additional information regarding the patient's overall medication therapy regimen. The pharmacist may be instructed to contact the appropriate medical provider to validate all medications listed in the physician recommended changes to the medication therapy regimen. If any of the recommendations are not accepted by the prescribing physician or the pharmacist performing the review, the pharmacist may be instructed to indicate the response and provide comments as to why the recommendations were not followed, as indicated at block 816, and to inform the medication therapy management services provider accordingly.

The pharmacist may be instructed to review the patient version of the Personal Medication Record with the patient during the consultation and to provide the patient version of the Personal Medication Record to the patient for future reference. If any of the recommended changes on the patient version of the Personal Medication Record are not accepted, the pharmacist may be instructed to make the appropriate changes on the patient version of the Personal Medication Record such that the patient's medication therapy regimen is accurately reflected. The pharmacist may also be instructed to review the Medication Action Plan with the patient and to provide the patient with the Medication Action Plan for future reference. If any of the recommended changes on the pharmacist version of the Personal Medication Record, the pharmacist may be instructed to make the appropriate changes on the Medication Action Plan so as to accurately reflect the patient medication therapy regimen. The pharmacist may further be instructed to answer all of the questions on the pharmacist satisfaction survey and to provide the answers to the medication therapy management services provider.

Although the medication therapy management routine and various methods associated therewith, as described herein, are implemented in software, it may be implemented in hardware, firmware, etc., and may be implemented by any other processor associated with the store and other facilities. Thus, the routine(s) described herein may be implemented in a standard multi-purpose CPU or on specifically designed hardware or firmware as desired. When implemented in software, the software routine(s) may be stored in any computer readable memory such as on a magnetic disk, a laser disk, or other storage medium, in a RAM or ROM of a computer or processor, etc. Likewise, the software may be delivered to a user or process control system via any known or desired delivery method including, for example, on a computer readable disk or other transportable computer storage mechanism or over a communication channel such as a telephone line, the Internet, etc. (which are viewed as being the same as or interchangeable with providing such software via transportable storage medium).

Although the forgoing text sets forth a detailed description of numerous different embodiments, it should be understood that the scope of the patent is defined by the words of the claims set forth at the end of this patent. The detailed description is to be construed as exemplary only and does not describe every possible embodiment because describing every possible embodiment would be impractical, if not impossible. Numerous alternative embodiments could be implemented, using either current technology or technology developed after the filing date of this patent, which would still fall within the scope of the claims.

Thus, many modifications and variations may be made in the techniques and structures described and illustrated herein without departing from the spirit and scope of the present claims. Accordingly, it should be understood that the methods and apparatus described herein are illustrative only and are not limiting upon the scope of the claims.

What is claimed is:

1. A non-transitory computer-readable medium having computer-executable instructions stored in a memory for implementing a method of determining the appropriateness of a medication and intervention, the computer executable instructions comprising instructions for:
   receiving medication data relating to a medication for a chronic medical condition associated with a person, wherein the medication comprises at least part of an actual medical treatment received by the person to treat the chronic medical condition;
   receiving treatment guidelines data relating to one or more treatment guidelines for treating the chronic medical condition, wherein the treatment guidelines pertain to established standards of care for the chronic medical condition including particular medication treatment for the chronic medical condition;
   evaluating the medication data and the treatment guidelines data to determine a level of compliance between the actual medical treatment being received by the patient and the one or more treatment guidelines, wherein the level of compliance is representative of the appropriateness of the medication treatment being received by the patient for the chronic medical condition;
   identifying an adverse health outcome for the person and determining a level of risk of the adverse health outcome associated with continuing the patient's actual medical treatment when the medication treatment does not comply with the one or more treatment guidelines;
   evaluating a likelihood of the identified health adverse health outcome occurring and the level of risk of the identified adverse health outcome to determine an intervention severity index representative of the urgency involved in intervening in the medical treatment of the person; and
   intervening in the medical treatment of the person in response to the risk of the identified adverse health outcome accordance with the intervention severity index, wherein an identified adverse health outcome having an intervention severity index greater than a predetermined threshold receives a different type of intervention than an identified adverse health outcome having an intervention severity index less than the predetermined threshold.

2. The non-transitory computer-readable medium having computer-executable instructions of claim 1, further comprising instructions for receiving medical condition data relating to a chronic medical condition associated with a person, wherein instructions for determining a level of compliance between the medication and the one or more treatment guidelines comprises instructions for evaluating the medication data, the medical condition data and the treatment guidelines data.

3. The non-transitory computer-readable medium having computer-executable instructions of claim 1, further comprising instructions for displaying a rationale for intervening in the medical treatment of the user, wherein the rationale is based on the treatment guidelines data.

4. The non-transitory computer-readable medium having computer-executable instructions of claim 1, wherein instructions for intervening in the medical treatment of the person comprises instructions for intervening in the medical treatment of the person during a refill of a prescription for the medication.

5. The non-transitory computer-readable medium having computer-executable instructions of claim 1, wherein instructions for intervening in a medical treatment of person comprises instructions for contacting one or more of the group consisting of: the person and a medical provider for the person.

6. The non-transitory computer-readable medium having computer-executable instructions of claim 1, further comprising instructions for determining a new medication for the person based on the treatment guidelines data, and wherein instructions for intervening in a medical treatment of the person comprises instructions for prescribing the new medication.

7. The non-transitory computer-readable medium having computer-executable instructions of claim 6, wherein instructions for determining a new medication for the person based on the treatment guidelines data comprises instructions for consulting with a medical provider associated with the person to determine the new medication.

8. The non-transitory computer-readable medium having computer-executable instructions of claim 1, wherein the chronic medical condition comprises at least one of the group consisting of: diabetes, heart failure, asthma and oral steroid use.

9. The non-transitory computer-readable medium having computer-executable instructions of claim 1, wherein the medication comprises at least one of the group consisting of: a statin, a beta blocker, an Ace-I inhibitor, an Angiotensin II receptor blocker, a long-term asthma controller and a bisphosphonate.

10. A non-transitory computer-readable medium having computer-executable instructions stored in a memory for implementing a method of determining the appropriateness of a medication and intervention, the computer executable instructions comprising:

receiving medication data relating to a medication for each of a plurality of persons, wherein the medication for each person comprises at least part of an actual medical treatment received by the person to treat a chronic medical condition;

receiving treatment guidelines data relating to one or more treatment guidelines for treating the chronic medical condition for each of the plurality of persons; and evaluating the medication data and the treatment guidelines data to identify one or more persons within the plurality of persons where the medication for each of the identified persons does not match with the treatment guidelines for the identified persons;

for each of the identified persons, determining a level of compliance between the actual medical treatment being received by the identified person and the one or more treatment guidelines, wherein the level of compliance is representative of the appropriateness of the medication treatment being received by the identified person for the chronic medical condition; and identifying an adverse health outcome for each identified person and determining a level of risk of the adverse health outcome associated with continuing the identified person's actual medical treatment when the medication treatment does not comply with the one or more treatment guidelines;

evaluating a likelihood of each identified health adverse health outcome occurring and the level of risk of each identified adverse health outcome to determine an intervention severity index for each identified person, wherein the intervention severity index is representative of the urgency involved in intervening in the medical treatment of the person; and intervening in the medical treatment of the person in accordance with the intervention severity index, wherein an identified adverse health outcome having an intervention severity index greater than a predetermined threshold receives a different type of intervention than an identified adverse health outcome having an intervention severity index less than the predetermined threshold.

11. The non-transitory computer-readable medium having computer-executable instructions of claim 10, further comprising instructions for receiving medical condition data relating to a chronic medical condition for each of the plurality of persons, wherein instructions for identifying one or more persons within the plurality of persons where the medication for each of the identified persons does not match with the treatment guidelines for the identified persons comprises instructions for evaluating the medication data, the medical condition data and the treatment guidelines data.

12. The non-transitory computer-readable medium having computer-executable instructions of claim 10, wherein instructions for identifying one or more persons within the plurality of persons where the medication for each of the identified persons does not match with the treatment guidelines for the identified persons comprises instructions for determining a level of compliance between the medication for each of the plurality of persons and the treatment guidelines for each of the plurality of persons.

13. The non-transitory computer-readable medium having computer-executable instructions of claim 10, further comprising instructions for intervening in a medical treatment of each of the identified persons when the medication for each of the identified persons does not match with the one or more treatment guidelines for each of the identified persons.

14. The non-transitory computer-readable medium having computer-executable instructions of claim 13, wherein instructions for intervening in the medical treatment of each of the identified persons comprises instructions for intervening in the medical treatment of each of the identified persons during a refill of a prescription for the medication of each of the identified persons.

15. The non-transitory computer-readable medium having computer-executable instructions of claim 13, wherein instructions for intervening in a medical treatment of each of the identified persons comprises instructions for contacting one or more of the group consisting of: the identified person and a medical provider for the identified person.

16. The non-transitory computer-readable medium having computer-executable instructions of claim 10, further comprising instructions for:
 determining a new medication for each of the identified persons based on the treatment guidelines data; and
 prescribing the new medication for each of the identified persons.

* * * * *